(12) United States Patent
Paul et al.

(10) Patent No.: US 7,559,942 B2
(45) Date of Patent: Jul. 14, 2009

(54) SPINE STABILIZATION SYSTEM

(75) Inventors: David C. Paul, Phoenixville, PA (US); Andrew Lee, Oreland, PA (US)

(73) Assignee: Globus Medical, Inc., Audubon, PA (US)

( * ) Notice: Subject to any disclaimer, the term of this patent is extended or adjusted under 35 U.S.C. 154(b) by 381 days.

(21) Appl. No.: 11/244,035

(22) Filed: Oct. 6, 2005

(65) Prior Publication Data
US 2006/0041259 A1 Feb. 23, 2006

Related U.S. Application Data

(63) Continuation of application No. 10/762,533, filed on Jan. 23, 2004, now Pat. No. 6,989,011, which is a continuation-in-part of application No. 10/443,755, filed on May 23, 2003, now Pat. No. 6,986,771.

(51) Int. Cl.
*A61B 17/70* (2006.01)
(52) U.S. Cl. ............... 606/250; 606/254; 606/257
(58) Field of Classification Search .......... 606/61, 606/60, 73, 250, 254, 257, 247, 248; 623/17.11, 623/17.16
See application file for complete search history.

(56) References Cited
U.S. PATENT DOCUMENTS

| | | | |
|---|---|---|---|
| 4,570,618 A | 2/1986 | Wu | |
| 4,773,402 A | 9/1988 | Asher et al. | |
| 5,180,393 A * | 1/1993 | Commarmond | 623/13.14 |
| 5,415,661 A | 5/1995 | Holmes | |
| 5,423,816 A * | 6/1995 | Lin | 606/61 |
| 5,649,925 A | 7/1997 | Barbera Alacreu et al. | |
| 5,672,175 A | 9/1997 | Martin | |
| 6,523,812 B1 | 2/2003 | Spinks et al. | |
| 6,986,771 B2 | 1/2006 | Paul et al. | |
| 6,989,011 B2 | 1/2006 | Paul et al. | |
| 7,329,258 B2 * | 2/2008 | Studer | 606/61 |
| 2003/0220643 A1 * | 11/2003 | Ferree | 606/61 |

FOREIGN PATENT DOCUMENTS

WO PCT/US2004/015922 11/2004
WO PCT/US2004/015922 12/2005

* cited by examiner

*Primary Examiner*—Pedro Philogene

(57) ABSTRACT

The invention generally concerns a spine stabilization system having one or more flexible elements having an opening or slit. The flexible element may be integrally formed in a rod having ends capable of receiving fasteners. The flexible element may limit rotation, flexion-extension, or lateral bending of the spine. The slit or opening may form helical pattern on the rod, and more than one slit or opening may be provided. The flexible element may be conformable to the natural spinal movement.

39 Claims, 20 Drawing Sheets

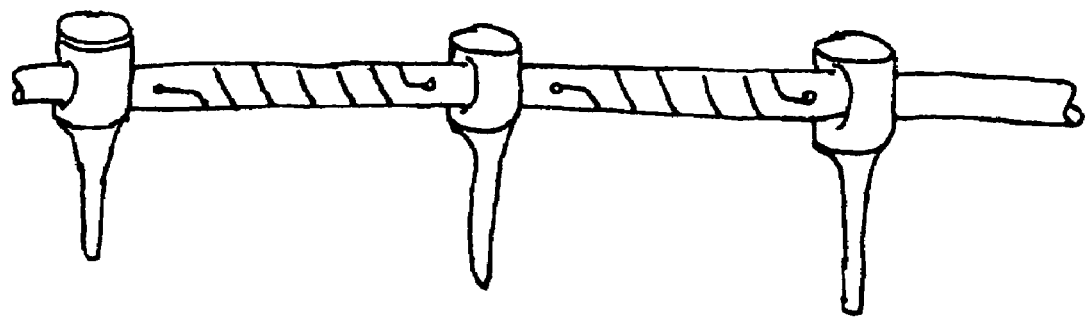
FIG. 29
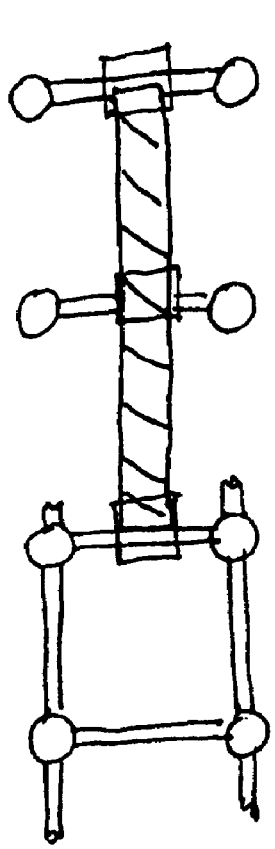 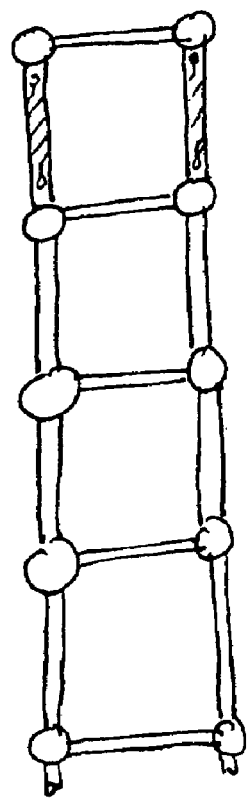
FIG. 30A FIG. 30B

FIG. 31A
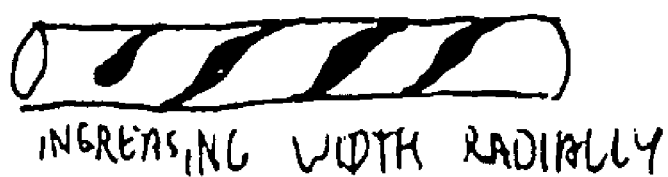
35 FIG. 31B
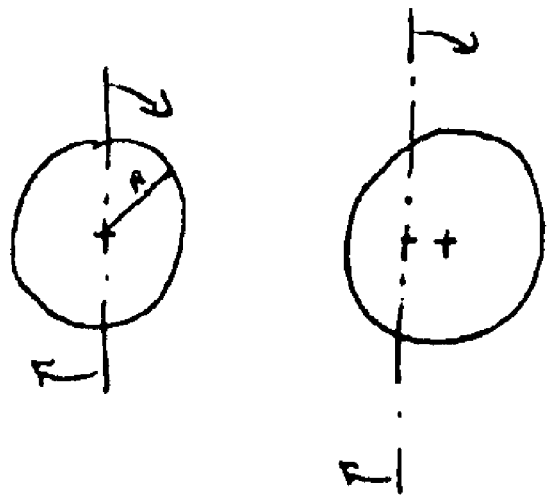
FIG. 32A  FIG. 32B

SPINE STABILIZATION SYSTEM

CROSS REFERENCE TO RELATED APPLICATIONS

This application is a continuation of U.S. application Ser. No. 10/762,533, filed on Jan. 23, 2004 now U.S. Pat. No. 6,989,011 which is a continuation in part of U.S. application Ser. No. 10/443,755, filed on May 23, 2003, now U.S. Pat. No. 6,986,771 the entirety of which is incorporated herein by reference thereto.

FIELD OF THE INVENTION

The present invention relates to soft stabilization systems for spinal motion segment units. In particular, the present invention is directed to a soft stabilization system including at least two bone fasteners and a flexible central portion conformable to the natural spinal movement.

BACKGROUND OF THE INVENTION

The spine includes a series of joints routinely called motion segment units, which is the smallest component of the spine that exhibits kinematic behavior characteristic of the entire spine. The motion segment unit is capable of flexion, extension, lateral bending and translation. The components of each motion segment unit include two adjacent vertebrae and their apophyseal joints, the intervertebral disc, and the connecting ligamentous tissue. Each component of the motion segment unit contributes to the mechanical stability of the joint.

Components of a motion segment that move out of position or become damaged can lead to serious pain and may lead to further injury to other components of the spine. Depending upon the severity of the structural changes that occur, treatment may include fusion, discectomy, or laminectomy.

Underlying causes of structural changes in the motion segment unit leading to instability include trauma, degeneration, aging, disease, surgery, and the like. Thus, rigid stabilization of one or more motion segment units may be an important element of a surgical procedure in certain cases (i.e., injuries, deformities, tumors, etc.), whereas it is a complementary element in others (i.e., fusion performed due to degeneration). The purpose of rigid stabilization is the immobilization of a motion segment unit.

As mentioned above, current surgical techniques typically involve fusing one or more unstable motion segment units and possibly, the removal of ligaments, bone, disc, or combinations thereof included in the unstable motion segment unit or units prior to fusing. There are several disadvantages to fusion, however. For example, the fusing process results in a permanent or rigid internal fixation of all or part of the intervertebral joints and usually involves metallic rods, plates, and the like for stabilization. In all cases, the systems are intended to rigidly immobilize the motion segment unit to promote fusion within that motion segment unit.

In addition to a loss of mobility, fusion also causes the mobility of the motion segment to be transferred to other motion segments of the spine. The added stresses transferred to motion segments neighboring or nearby the fused segment can cause or accelerate degeneration of those segments. One other disadvantage to fusion is that it is an irreversible procedure. In addition, it is believed that fusion of a motion segment has a clinical success of approximately 70 percent, and often does not alleviate pain experienced by the patient.

Thus, while such fusion systems have been used since the early 1960's, the intentionally rigid designs have often caused stress concentrations and have directly and indirectly contributed to the degeneration of the joints above and below the fusion site (as well as at the fusion site itself). In addition, rigid, linear bar-like elements eliminate the function of the motion segment unit. Finally, removal of portions of the motion segment unit reduces the amount of support available for the affected motion segment unit.

Fusion procedures can be improved by modifying the load sharing characteristics of the treated spine. Thus, it would be desirable to allow more of a physiologic loading between pedicular fixation and anterior column support. It would also be desirable to have a device that precludes or at least delays the need for fusion for all but the most advanced degeneration of a motion segment, particularly if such a device would allow close to normal motion and pain relief.

Thus, a need exists in the art for a soft spine stabilization system that replicates the physiologic response of a healthy motion segment.

SUMMARY OF THE INVENTION

The present invention is generally directed towards a flexible spinal stabilization system that can provide load sharing either as an enhancement to a fusion device or as a motion-preserving non-fusion device.

One embodiment of the invention relates to a novel flexible prosthesis for intervertebral or intersegmental stabilization designed to load share with a graft in the anterior column that allows for graft resorption while ensuring compressive loading on the graft for fusion procedures in the spine.

Another embodiment of the invention is directed towards a novel prosthesis for intervertebral or intersegmental stabilization designed to ensure proper alignment and motion between vertebrae of the spinal column that helps partially unload the discs and facet joints to give pain relief.

One embodiment of the invention relates to a flexible spine stabilization system having a first flexible element with a tubular structure that has at least one slit formed in it, and a second flexible element disposed within the first flexible element. The second flexible element also has a tubular structure with at least one slit formed in it. One or more fasteners may be connected to or in communication with one of the flexible elements.

The slit or slits formed on either or both of the tubular structures may form a generally helical pattern around a longitudinal axis of the tubular structure. In one embodiment having one flexible element disposed within another, a helical pattern on one tubular structure of one flexible element travels in the opposite direction as a helical pattern on another tubular structure of another flexible element. The flexible elements of the invention may be straight or curved in a neutral position to accommodate the lordosis in the spine.

Several embodiments of the invention relate to the degree to which the flexible elements permit rotation, flexion-extension, lateral bending, or axial compression. For instance, in one embodiment of the invention movement of a first end of a flexible element relative to a second end is limited to a range of from about 1° to about 30° in all planes. In another embodiment, the range of motion is limited to a range of from about 0° to about 3° in all planes.

One embodiment of the invention limits rotation of a first end of a flexible element relative to a second end to a range of from about 1° to about 30°, while in another embodiment the range is limited from about 1° to about 6°. In yet another embodiment, rotation is limited to a range of from about 0° to about 3°. In another embodiment, the flexible element prevents rotation of the first end relative to the second end.

Another embodiment limits flexion-extension of a first end of a flexible element relative to a second end to a range of from 0° to about 30°. Alternatively, the range of flexion-extension may be limited to a range from about 0° to about 3°, and in yet another embodiment the range may be from about 3° to about 30°.

Lateral bending of a first end of a flexible element relative to a second end likewise may be limited to a prescribed range. For instance, in one embodiment lateral bending is limited to a range about 0° to about 30°, while in another embodiment it is limited from about 0° to about 3°. In yet another embodiment, lateral bending of the flexible element is limited to a range from 3° to about 30°.

In one embodiment, the first flexible element limits axial compression of a first end of a flexible element relative to a second end to a range from about 0 mm to about 7 mm. In another embodiment, axial compression is limited to a range from about 0.5 mm to about 7 mm, while in another embodiment it is limited from about 0 mm to about 1 mm.

Locking mechanisms may be used in any of the embodiments of the invention. Thus, in one embodiment of the invention a locking mechanism may secure one or more flexible elements in a rigid configuration. One benefit of this feature, for example, is that the surgeon may have flexibility of the system when positioning the components to avoid bony anatomy, but then be able to make the system more rigid once the component is in its desired position or configuration. In one embodiment, the locking mechanism comprises a cable disposed within a flexible element. The cable can be tensioned to secure one or more flexible elements in a rigid configuration. In another embodiment, the locking mechanism comprises a cable disposed outside of said a flexible element, and as the cable is tensioned it secures one or more flexible elements in a rigid configuration.

In one embodiment of the invention, a solid rod is disposed within the tubular structure of a flexible element to increase the stiffness of the flexible element.

The flexible element of the invention may be used to as part of various components of a spine stabilization system. For instance, the flexible element may form all or part of one or more rods. In another embodiment, the flexible element may also form at least part of a transconnector. Depending on what component of the spine stabilization system uses the invention, fasteners may also be connected to the component. For instance, in one embodiment the flexible element is connected to bone fasteners, such as pedicle screws or the like.

BRIEF DESCRIPTION OF THE DRAWINGS

FIG. 29 is a side view of a rod of the present invention having a plurality of flexible elements integrally formed therein;

FIGS. 30A and 30B are illustrations of stabilization systems of the present invention;

FIGS. 31A and 31B are illustrations of how the width of a cut, slit, opening, or thread may be varied either axially, radially, or both; and FIGS. 32A and 32B illustrate variations of how a cut, slit, opening, or thread may be formed.

DETAILED DESCRIPTION OF THE INVENTION

Figure 1:
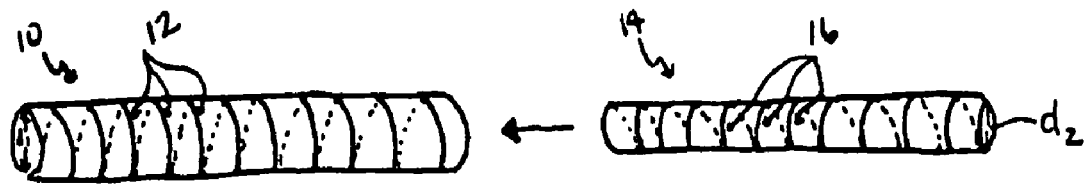
FIG. 1 is a side view of a flexible central portion according to an embodiment of the invention.

The present invention is directed to flexible stabilization systems for use with the anterior, antero-lateral, lateral, and/or posterior portions of at least one motion segment unit of the spine. The systems of the invention are designed to be conformable to the spinal anatomy, so as to be less intrusive to surrounding tissue and vasculature than existing solid stabilization systems.

The system of the invention is contemplated to be used on the cervical, thoracic, lumbar, and/or sacral segments of the spine. For example, the size and mass increase of the vertebrae in the spine from the cervical to the lumbar portions is directly related to an increased capacity for supporting larger loads. This increase in load bearing capacity, however, is paralleled by a decrease in flexibility and an increase in susceptibility to strain. When rigid immobilization systems are used in the lumbar segment, the flexibility is decreased even further beyond the natural motion restriction of that segment. Replacing the conventional rigid immobilization systems with the present invention restores a more natural movement and provides added support to the strain-susceptible area.

One embodiment of the spine stabilization system of the present invention includes at least two bone fasteners and at least one flexible element. The flexible element advantageously provides desirable properties for bending or twisting that allows the system to accommodate natural spine movement. As used herein, a flexible element preferably approximates or resembles a relatively circular tube or rod. A flexible element may have other shapes as well. For instance the flexible element may have a cross-section that approximates or resembles a circle, an oval, an ellipse, or angular geometric shapes such as triangles, squares, rectangles, trapezoids, or the like.

In one embodiment, a central portion of at least one component of the flexible element may be hollow. As mentioned above, for instance, part of the flexible element may resemble a hollow tube. A skilled artisan would appreciate that there are several ways to form a hollow tube, regardless of whether it is circular or has any other cross-sectional shape. For example, the tube may be formed by extruding a material, such as metal or polymeric materials, through a die. One or more slits may then be cut into the extruded material. For instance, a tube may have a helical spiral slit cut along at least a portion of the tube. Alternatively, the tube may have a plurality of diagonal slits cut into its surface. The slits may be machined into the tube, such as by turning the tube on a lathe, by milling the slits, using a wire EDM, or by other suitable methods.

The tube may also be formed from winding one or more flat strips of material. For instance, a thin strip of metal may be wound in a generally spiral or helical shape in order to form a tube. The distance between a first edge of the strip and a second edge forms a helical slit along the flexible element. The helical slit may be continuous along the entire length of the flexible element or may be formed on only a portion of the flexible element, such as at the center or on one side.

The following examples describe embodiments using a flexible rod, tube, or other structure. It should be understood that in these examples the different types of flexible elements described herein may be replaced or interchanged with a flexible element having different shapes or configurations, including the many variations described herein.

The present invention may also be used as a cross-brace or transconnector in communication with two rods along a portion of the length of the spine. It is well known that the strength and stability of a dual rod assembly can be increased by coupling the two rods with a transconnector that extends across the spine in a direction that is generally perpendicular to the longitudinal axes of the rods. When used as a transconnector, the present invention includes a first fastener connecting the transconnector to a first rod and a second fastener connecting the transconnector to a second rod. Alternatively, the transconnector may be connected to one or more bone fasteners associated with a rod. Examples of transconnector designs that may be improved by the present invention are described in U.S. Pat. No. 5,743,911 to Cotrel, U.S. Pat. No. 5,651,789 to Cotrel, U.S. Pat. No. 6,139,548 to Errico, U.S. Pat. No. 6,306,137 to Troxell, U.S. Pat. No. 5,947,966 to Drewry, U.S. Pat. No. 5,624,442 to Mellinger, and U.S. Pat. No. 6,524,310 to Lombardo, all of which are incorporated herein in their entirety.

When a flexible element of the present invention is included in a transconnector design, it is preferred that the flexible element can be selectively made substantially rigid once the transconnector is in its desired position. The ability to selectively make the flexible element substantially rigid may also be desirable in other applications of the invention in addition to transconnectors. The flexible element initially allows the surgeon to bend or twist the transconnector as needed to connect or associate the transconnector to the first and second rods. One advantage of this feature of the invention is that the flexible portion allows the surgeon to reposition or change the shape of the transconnector in order to avoid interfering with bony anatomy and then make the transconnector rigid in order to securely prevent movement of the first rod relative to the second rod.

As explained in greater detail below, the flexible element can be configured in many different ways. For instance, the flexible element may be a relatively straight rod, tube, or plurality of rods and/or tubes, such as shown in FIG. 1. Alternatively, the flexible element may have a curved shape that corresponds approximately to the natural curvature of the portion of the spine that it supports. In each embodiment, the flexible element may be made of one or more tubes that are configured to allow the element to flex, bend, or twist. For instance, a tube may be formed with slits or other openings that increase the flexibility of the tube. The slits may form a helical, spiral, or thread-like pattern on the tube, may form a pattern along a portion of the tube. The slits also may be on only a portion of the circumference of the tube to provide greater flexibility for a limited range of motion. If more than one tube is used, the wall thickness of each tube may be varied in order to achieve a desired response to bending or torsional forces.

The Flexible Element

The flexible element of the system of the invention provides stability, strength, flexibility, and resistance without the traditional rigidity of prior systems. While the flexible element may be designed in a variety of ways according to the invention, the types of design may differ depending on the final implementation of the system, i.e., lateral, posterior, etc.

Figure 2:
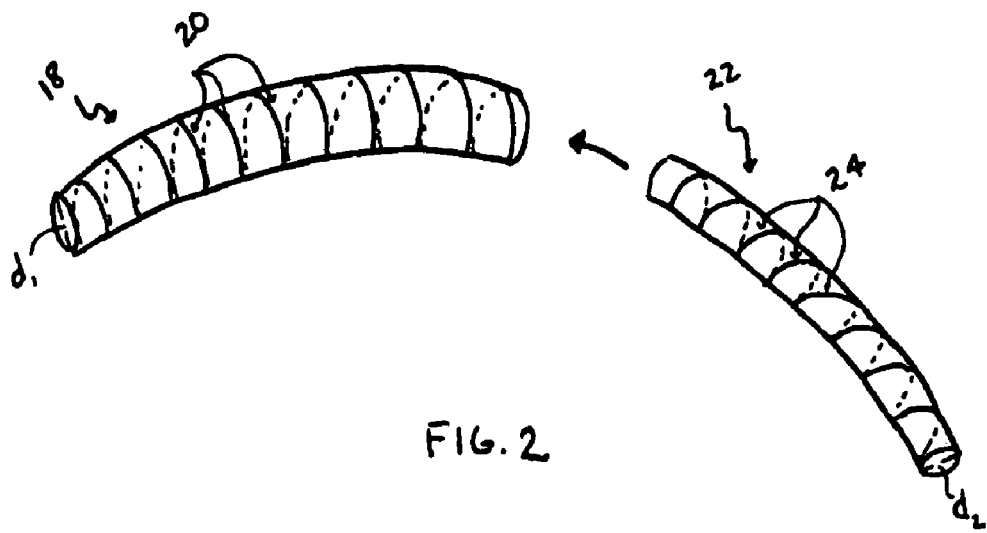
FIG. 2 is a side view of a curved flexible central portion according to another embodiment of the invention.

In a posterior application, for example, the flexible element may include a straight or curved rod having a double helical pattern. FIGS. 1 and 2 show non-limiting examples of the flexible element of the invention. In FIG. 1, for example, the flexible element includes a first rod 10 having a first spiral pattern and a first diameter ($d_1$) and a second rod 14 having a second spiral pattern and a second diameter ($d_2$). Reference numerals 12 and 16 refer to the edge of the flexible portion that forms the generally spiral-shaped pattern.

In some embodiments, the edge of the material forming one side of the spiral pattern abuts or contacts the edge of the material on the opposing edge of the spiral. The flexible element also may be configured and adapted such that the contact between these two edges exhibits preload forces even when the flexible portion is not undergoing externally applied torsional, axial, or bending loads. In other words, the contact between the opposing edges causes each edge to apply loading to opposing edge.

This preloaded configuration may be beneficial for designing a preferential response to different types of external forces or loading. For instance, a preloaded flexible element may provide a greater resistance to torsional loads that would tend to further tighten the flexible element due to added frictional forces resisting sliding movement of the edges against each other. Thus, a preloaded flexible element may provide a system that has at least about 1.2 times greater resistance to torsional loads in one direction than in an opposite direction. In one embodiment, a preloaded flexible element may provide at least about 1.4 times greater torsional resistance in one direction than another. Portions of one or both of the first and second rods may utilize a preloaded configuration to create a preferential response to certain loads.

In other embodiments of the invention at least a portion of the material forming the edge of one side of the spiral pattern may not contact the material forming the edge of the opposing side of the spiral. The gap or space between the opposing edges of the spiral pattern further increases the ability to custom tailor a system response to different types or locations of forces or loads applied to the system. The placement of gaps in the spiral may permit the stabilization system to deflect or bend in a manner similar to normal motion of the segment unit. Moreover, the width of the space between the opposing edges of the spiral may be non-uniform in order to permit bending in one direction while resisting bending in another. For example, from about 30 to 85 percent of the circumference of the rod may have spaces or gaps permitting lateral or forward bending but limiting hyperextension of the segment in a rearward direction. More preferably, the spaces or gaps between the edges of the material defining the spiral pattern are on about 40 to about 60 percent of the circumference of the rod.

A second rod may be secured in place with respect to the first rod in any suitable manner. Preferably, the second rod is substantially prevented from moving in an axial direction out of its desired position relative to the first rod. This preferred configuration can be accomplished in several ways. For example, the second rod may fit snugly within the first rod in a manner that the interference fit or press fit prevents sliding or movement of the second rod in an axial direction relative to the first rod.

When the first and second rods are secured together, such as by an interference fit, the outer diameter of the second rod ($d_2$), when not subjected to external loading and prior to assembly, may be slightly larger than the inner diameter of the first rod. Preferably, the second rod has an outer diameter that is about 102% to about 105% larger than the inner diameter of the first rod. Alternatively, the outer diameter of the second rod may be from about 0.001 to about 0.010 inch greater than the inner diameter of the first rod. During assembly, the first rod may be expanded or the second rod may be contracted so that the second rod can be placed within the first rod. Alternatively, both diameters of the first and second rods may be altered during assembly. The diameters may be altered in a number of ways. For instance, torsional forces may be applied to the second rod to cause its outer diameter to decrease. Additionally, the second rod may be stretched or extended along its axis in order to reduce its outer diameter during assembly. Likewise, torsional forces may be applied to the first rod in a direction that causes the spiral patters to partially unwind or open while the second rod is being positioned inside it.

Alternatively, the inner diameter of the first rod may be expanded by elevating its temperature during assembly. For example, the temperature of the first rod may be elevated during assembly. Similarly, the outer diameter of the second rod may be reduced by lowering its temperature.

In yet another embodiment of the invention, the second rod is fitted inside the first rod simply by applying axial loads to the second rod in order to force it inside the first rod.

In another embodiment, the first and second rods are secured together by applying a weld, adhesive, epoxy, or the like to a portion of the rods.

It is not required, however, that the first and second rods are assembled using a press fit or interference fit. For example, the rods may be secured together by a pin placed through at least a portion of both first and second rods. In yet another embodiment the first and second rods may be configured and adapted such that the first and second rods have threading on at least a portion of their interior and exterior surfaces. The threaded portion of the outer surface of the second rod may then be threaded onto the interior threading of the first rod. Additionally, the first and second rods may be secured together by applying a clamp to at least a portion of the first rod that surrounds the second rod.

When an interference fit is not utilized to secure the first and second rods together, the second rod may have an outside diameter that is less than the inside diameter of the first rod. This may not only facilitate easy assembly of the rods, but also may provide greater flexibility in response during bending or deflection. In one embodiment, $d_2$ is about 98 percent or less of $d_1$. In another embodiment, $d_2$ is about 95 percent or less of $d_1$. In still another embodiment, $d_2$ is about 90 percent or less of $d_1$. One of ordinary skill in the art would appreciate that while a larger difference between the two diameters would generally result in greater flexibility of the flexible central portion, such differences may also lead to less stability of the central portion because of the potential of the second rod to slip within the first rod. Thus, it is preferred that the difference in diameters be such that the stability of the central portion is sufficiently maintained.

In FIG. 2, the flexible element includes a first rod 18 curved in an arc-type shape and a second rod 22 also curved in a similar arc-type shape, wherein the second rod 22 is inserted into the first rod 18. As in FIG. 1, at least a portion of the rods have edges that define a generally spiral shaped pattern. As described above, the opposing edges of the rod defining the pattern may contact each other with or without preload forces. Alternatively, the edges defining the pattern may be spaced apart from each other.

The first and second spiral patterns preferably travel in opposite directions along the first and second rods. One benefit of this configuration is that it allows greater flexibility in balancing a response to torsional forces applied to the assembly of rods. If the patterns on both rods travel in the same direction, it may be difficult to achieve a balanced, or neutral, response to torsional forces applied in different directions because resistance to torsional forces causing the spiral to unwind may differ from resistance to torsional forces causing the spiral to be wound more tightly.

As illustrated above, there are many parameters of the invention that may be adjusted to create a desired response under different types of loading. One design parameter includes the wall thicknesses of the first and second rods. For example, if a balanced or neutral response to torsional loading is desired, regardless of which direction the torque loading is applied, the wall thickness of the first rod may be slightly greater than the wall thickness of the second rod. Varying the wall thickness of the first and second rods also may allow the assembled rods to respond differently to torsional loads in different directions.

In one embodiment, both the first and second rods 10, 14 are formed having the same material thickness. In another embodiment, the first and second rods 10, 14 have different material thicknesses. For example, the first rod 10 may be thicker than the second rod 14 for more outer stability. In contrast, the second rod 14 may be thicker than the first rod 10 to allow the flexible central portion to have more inner stability. In this aspect of the invention, the thickness of the first rod ($t_1$) may differ from the thickness of the second rod ($t_2$) by about 1 percent or greater. In one embodiment, $t_1$ and $t_2$ differ from each other by about 5 percent or more. In another embodiment, $t_1$ and $t_2$ differ from each other by about 10 percent or more.

Figure 3:
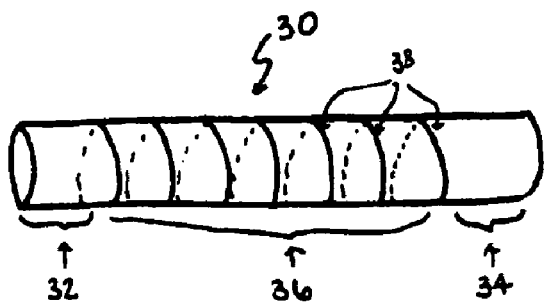
FIG. 3 is a side view of a flexible central portion having solid end segments according to an embodiment of the invention.

The spiral pattern may be designed to have portions of solid or rigid areas along the rod. For example, because the flexible central portion is ultimately attached to bone fasteners, the end portions of the flexible central portion may be solid or rigid whereas the middle portion has the double helical pattern shown in FIGS. 1 and 2 or is made flexible using any other feature or configuration described herein. FIG. 3 illustrates one such embodiment. The flexible central portion 30, having an overall length L, has end portions 32 and 34 having lengths $L_1$ and $L_2$ and a middle portion 36 having a length $L_3$. The end portions 32 and 34 may be left as solid or uncut material to avoid depressing or detenting the material when the bone fasteners are attached. The appropriate length of the end portions 32 and 34 may be designed to accommodate particular bone fasteners. For example, in one embodiment, end portions 32, 34 may have lengths ($L_1$, $L_2$) of about 30 percent or less of the flexible central portion 30. In another embodiment, $L_1$ and $L_2$ may be about 15 percent or less of the flexible central portion 30. In still another embodiment, $L_1$ and $L_2$ are each about 5 percent or less of the total length (L) of flexible central portion 30.

In addition to describing the length of end portions 32 and 34 relative to the flexible element, they also may be defined in absolute terms. For example, the end portions may be about 1.5 cm or less in length. In another embodiment, the lengths of end portions 32 and 34 may be about 1.0 cm or less, or even may be only about 0.5 cm or less. The lengths of $L_1$ and $L_2$ need not be the same. For example, one end portion 32 may have a length of about 30 percent or less of the flexible central portion, which the other end may be best described as being only about 0.5 cm or less in length. Thus, it is not required that both end portions meet any one range.

When the end portions are solid or rigid, the middle portion 36 of the flexible element 30 becomes the "flexible" segment. The middle portion 36 may make up about 60 percent or greater of the flexible central portion, preferably about 80 percent or greater. In one embodiment, the length of the middle portion ($L_3$) is about 90 percent or greater of the total length of the flexible central portion. In other words, the ratio of $L_3$ to $L_1+L_2$ is preferably about 3:2, more preferably about 4:1. And, in one embodiment, the ratio of $L_3$ to $L_1+L_2$ is about 9:1. In one embodiment of the invention, however, the entire length of the rods is flexible. In this embodiment, the lengths of $L_1$ and $L_2$ are zero.

Figure 3A:
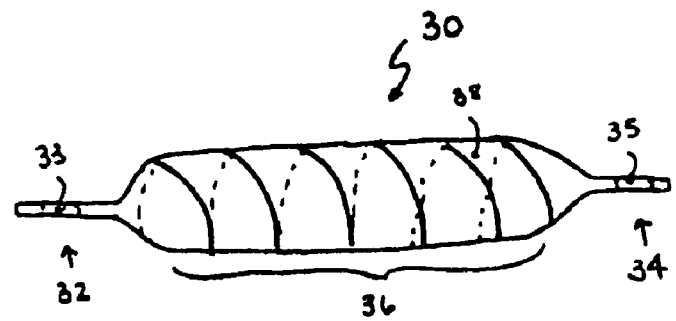
FIG. 3A is a side view of the flexible central portion shown in FIG. 3 having flattened solid end segments according to an embodiment of the invention.
Figure 3B:
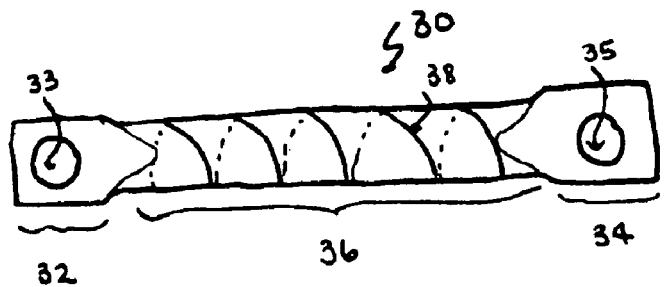
FIG. 3B is a top view of the flexible central portion shown in FIG. 3 having flattened solid end segments with eyelets therein according to an embodiment of the invention.

In addition, after the flexible element is assembled, either with a single rod or two rods (as described above), the solid or rigid ends may be flattened and punched with eyelets. As shown in FIGS. 3A and 3B, the ends 32 and 34 are flattened and eyelets 33 and 35 are punched so as to allow attachment to the bone fasteners, e.g., screws may be inserted through the eyelets 33 and 35. The middle portion 36 remains cylindrical and flexible.

As mentioned above, there are numerous design parameters for the spiral patterns on the rods, such as the amount of preloading, contact, or spacing between the edges that define the spiral. The size, location, and number of spaces in the spiral enables one to fine tune the flexibility of the flexible central portion. As understood by those of ordinary skill in the art, an increase in the size of the empty spaces and/or number of empty spaces in the spiral pattern will have a direct effect on the flexibility and stability of the central portion. For example, a spiral pattern having fewer and/or smaller spaces or gaps will be more rigid in comparison to a spiral pattern having larger and/or larger spaces.

In one embodiment, the spaces or gaps (12, 16, 20, 24, 38) between each solid segment is about 0.01 percent or greater of the total length (L) of the flexible central portion. In another embodiment, each empty space is about 0.1 percent or greater of the total length (L) of the flexible central portion. In still another embodiment, each empty space is about 1 percent or greater of the total length (L) of the flexible element. The ratio of each empty space 42 (FIG. 4) to the two solid portions flanking the empty space (44) is preferably about 1:4 to about 1:128. In another embodiment, the ratio of an empty space 42 to the two solid portions (44) on either side of the empty space 42 is about 1:8 to about 1:128. In still another embodiment, the empty space to solid portions ratio is about 1:32 to about 1:128.

Figure 4:
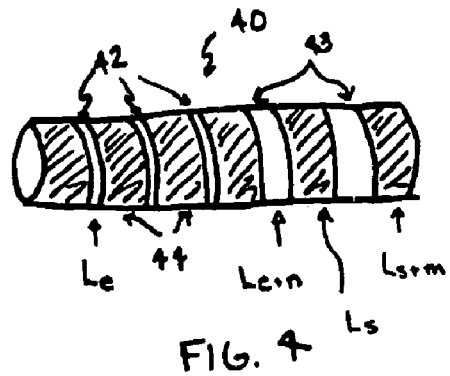
FIG. 4 is a side view of a flexible central portion with varying sizes of empty spaces between solid portions of the spiral pattern according to an embodiment of the invention.

Assuming that the spiral pattern continues the length of the flexible element, i.e., has no solid or rigid ends as discussed above in FIG. 3, the spiral pattern in the flexible element 40 has a number of empty spaces, openings, or slits 42 (e) and a number of solid portions 44 (s) flanking the empty spaces (FIG. 4). For example, the flexible element 40 may have a number of solid portions, wherein all of the solid portions together make up about x percent or greater of the axial length of the flexible element. The remaining 100−x percent or less of the total axial length (L) of the flexible element 40 is accounted for in the empty spaces 42 between the solid portions 44. If all solid portions 44 were the same with respect to each other (all equal of $L_s$), the length of each solid portion ($L_s$) with respect to the overall length (L) of the flexible central portion 40 would be equal to 0.80*L/s. Similarly, if the width of each slit was the same as the other slits (all equal to $L_e$), the length of a slit opening ($L_e$) with respect to the overall length (L) of the flexible element 40 would be equal to [(1.0−x)*L]/e. Therefore, the ratio of the width of a slit to the widths of its two adjacent solid portions would be equal to {[(1.0−x)*L]/e}/(0.80*L/s).

Figure 4A:
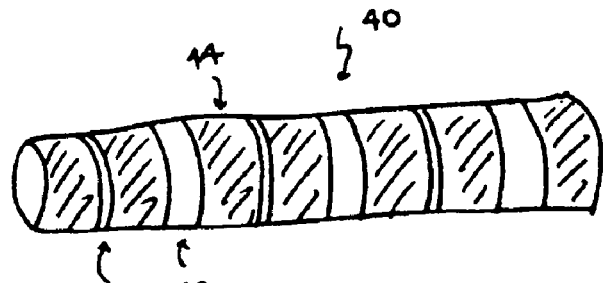
FIG. 4A-C is a side view of a flexible central with varying sizes of empty spaces and solid portions of the spiral pattern according to an embodiment of the invention.

And, while a consistent spiral pattern may be used for the flexible element, the invention also includes spiral patterns with differing widths of the empty spaces 12, 16, 20, 24, and 38 of the slit openings. These differences may appear random in nature, localized, or patterned. FIG. 4 demonstrates one variation of this concept. The slit openings 42 have a first length ($L_e$), while the slit openings 43 have a greater length, denoted by $L_{e+n}$. if each solid portion 44 may be the same as the next solid portion in length (all equal to $L_s$). In another embodiment (FIG. 4A), all of the solid portions 44 are equal with respect to each other, but the slit openings 42 and 43 differ with respect to each other so that the variance is one where every other empty space 43 is twice the length of the nearest empty space 42.

Figure 4B:
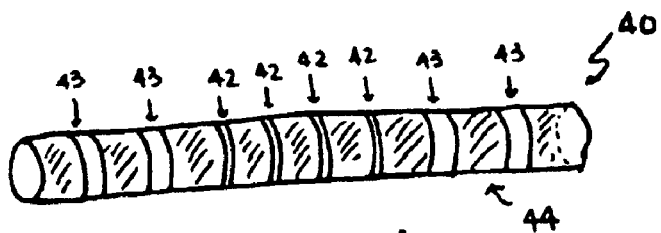
Figure 4C:
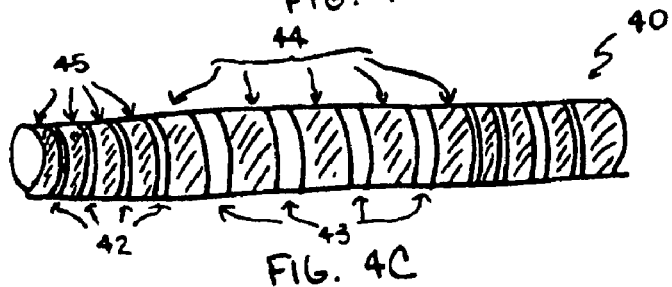

In yet another embodiment (FIG. 4B), the slit openings 43 towards the ends of the flexible element 40 are larger than the slit openings 42 near the middle of the flexible element 40. In contrast, the slit openings near the middle of the flexible element 40 may be larger than the slit openings near the ends (not shown). In still another embodiment, both the solid portions 44 and the slit openings 42 are varied in size. As shown in FIG. 4C, the solid portions 45 near the ends of the flexible element 40 may be smaller in comparison with the solid portions 44 near the middle of the flexible element and, likewise, the slit openings 42 near the ends of the flexible element may be smaller in comparison with the slit openings 43 near the middle of the flexible element.

In another embodiment (not shown), the solid portions near the middle of the flexible element may be larger than the solid portions at the ends of the flexible element and, similarly, the slit openings near the middle of the flexible element may be larger than the slit openings at the ends of the flexible element. Another variation on this concept would involve a flexible element wherein the solid portions at the ends are larger than the solid portions in the middle of the flexible element, and wherein the slit openings at the middle of the flexible element may be larger than the slit openings at the ends. The opposite design is also contemplated: the solid portions at the ends may be smaller than the solid portions in the middle of the flexible element, and the slit openings at the middle of the flexible element may be smaller than the slit openings at the ends. While no generic equations are provided herein to describe such designs, those of ordinary skill in the art presented with the teaching of the previous invention would be capable of determining the size of the slit openings 42 and solid portions 44 to accomplish a desired flexibility and stability.

Figure 5A:
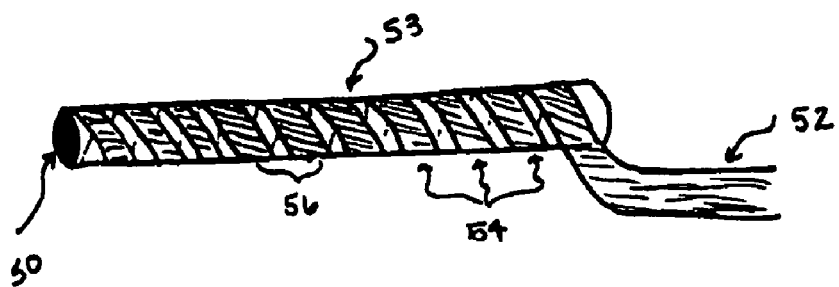
FIG. 5 illustrates a method of forming the flexible central portion of the invention by wrapping material into a spiral pattern.
Figure 5B:
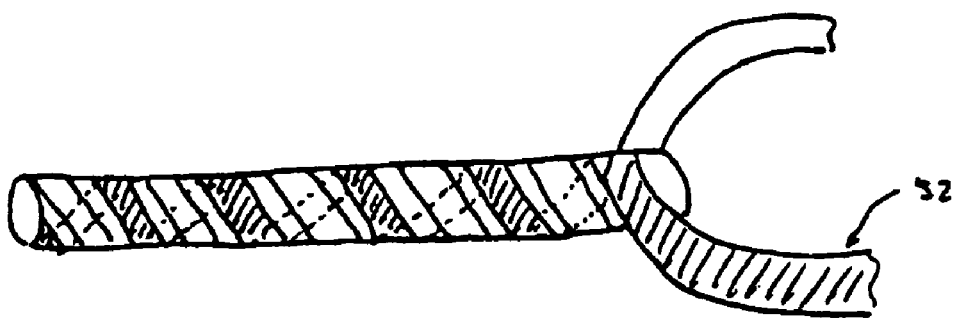

The flexible element generally described with respect to FIGS. 1 and 2 may be fabricated in a variety of ways. For example, FIG. 5A illustrates one suitable method for constructing the flexible element of the invention. A strip of material 52 may be wound about a forming rod 50 to create a first flexible element 53 having a desired spiral pattern. Additionally, as shown in FIG. 5B, the flexible element may be formed by winding two strips of material around a forming rod such that one side of the helical pattern is from a first strip while the opposing side is from the second strip. The helical pattern could also be formed by an even greater number of strips of material.

Once formed, the first flexible element 53 has slit openings 54 and solid portions 56 as described above, which may vary in size and number depending on the tightness of the spiral desired. This first flexible element 53 may be used alone as the sole flexible element in the system of the invention. In another embodiment, however, a second flexible element may be formed using a similar method, wherein the diameter of the second flexible element is less than the diameter of the first flexible element 53 so that the second flexible element fits inside the first. Another way of forming the flexible element would be to form the first flexible element 53 using a forming rod 50, and then forming a second flexible element directly on top of the first flexible element 53 (while still on the rod) using an opposite winding pattern to create the double helical pattern. The rod 50 may then be removed and the flexible element may be cut into discrete sections if necessary.

Figure 5C:
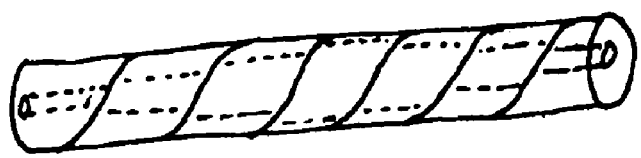
Figure 5C:
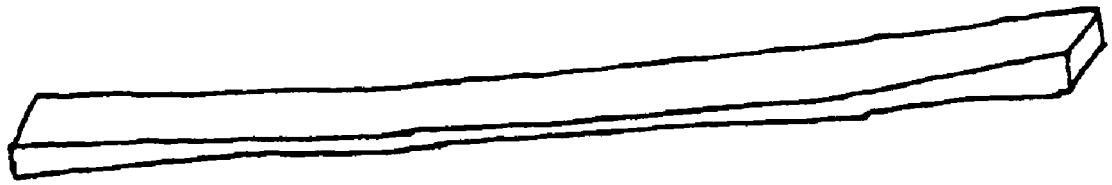
Figure 5C:

Referring to FIG. 5C, the strips used to form a tube may vary in thickness along their length. In this manner, the tube would exhibit varying flexibility and torsion resistance along its length. For instance, if it is desired that the center or mid-section, portion or region of the flexible element have the greatest flexibility or the least torsion resistance, the thickness of the strip used to form this part of the flexible element may be reduced. In another embodiment, the strip may also have a slot or opening machined or cut into it along at least a portion of its length to provide even greater flexibility. In embodiment, at least one strip has a slot or opening formed in about 20 to about 80 percent of the length of the strip. In another embodiment, the slot formed on the strip is from about 30 to about 60 percent of the length of the strip, and in yet another embodiment, the slot is from about 40 to about 50 percent of the length of the strip. Preferably, the slot is located approximately at the middle of the strip.

More than one slot may be formed in the strip. For instance, it may be beneficial to provide a slot near each end of the strip. Additionally, the width of the slot or slots may be varied along the length of the strip. For example, a single slot positioned near the middle of the strip may be 1.3 times wider at the middle of the slot than at the ends. In another embodiment, the middle of the slot is about 1.5 times wider than the ends.

Figure 6:
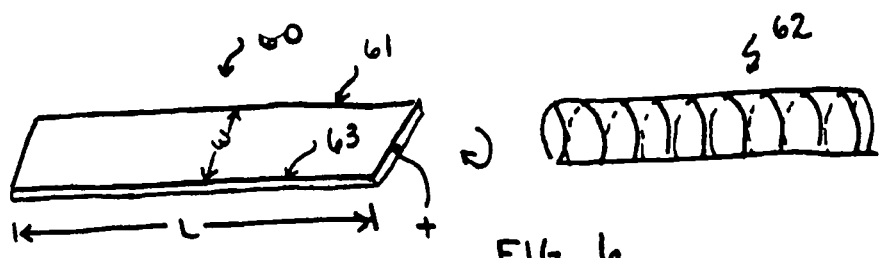
FIG. 6 illustrates a method of forming a flexible central portion according to one aspect of the invention.
Figure 7:
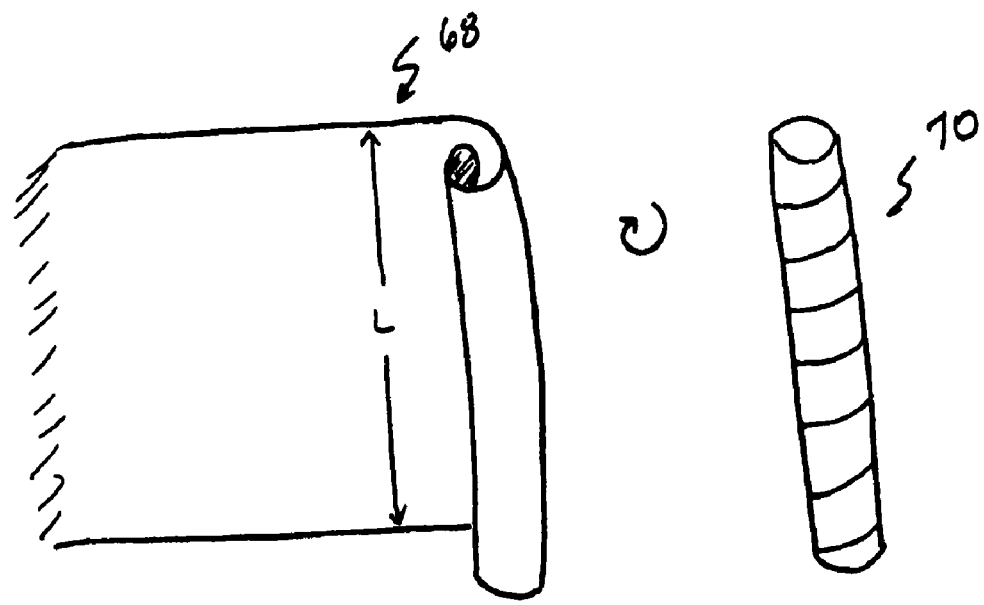
FIG. 7 illustrates a method of forming a flexible central portion according to one aspect of the invention using a sheet of material rolled to form a cylinder.

Another method of forming the flexible element of the invention includes obtaining a piece of material having at least a known width (w) and a known thickness (t) (FIG. 6), and bending the material 60 so that the ends 61 and 63 meet to form a generally cylindrical tube. The ends 61 and 63 may be fused, soldered, or otherwise joined (depending on the material 60) to form a rod. In addition, as shown in FIG. 7, the flexible element may be formed from a sheet of material 68 that is rolled, crimped, and cut to form a rod or tube. The spiral pattern may then be formed in the pre-formed rod or tube by turning it on a lathe, mill cutting, laser cutting, water jet cutting, wire EDM cutting, or combinations thereof. In one embodiment, the length (L) of the material 60, 68 is known before the material is formed into the rod to eliminate the additional step of cutting the tube or rod after forming.

In another embodiment, however, mass production may be accomplished by forming a long tube or rod, cutting the spiral pattern in the tube or rod, and then severing it at predetermined intervals to form the flexible element of 62, 70. As discussed above, a second tube or rod having a smaller diameter may be formed in the same manner and inserted into the first tube having a larger diameter to form the flexible element 62, 70.

Figure 8:
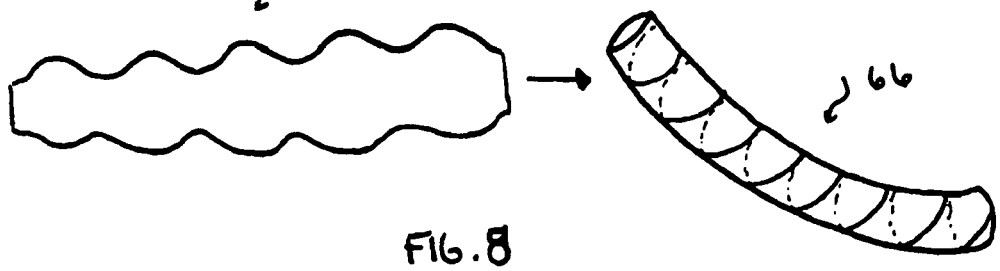
FIG. 8 illustrates a method of forming a curved flexible central portion according to an embodiment of the invention.

To form the pre-curved flexible element of FIG. 2, the material 68 may be die cut or stamped having a curvilinear pattern in the footprint (FIG. 8). Once wound into a spiral, the curved flexible element 70 results. As shown in FIG. 8, the width of the strip can be varied such that the flexible portion of the strip corresponding to the outermost side (i.e. the part of the flexible portion farthest away from the radius of curvature) of the curved portion has a width a and the innermost side of the curved portion has a width β. The length x of FIG. 8 corresponds to the circumference of the rod. The ratio of a to β for any length x governs the radius of curvature for that part of the flexible portion.

Figure 9:
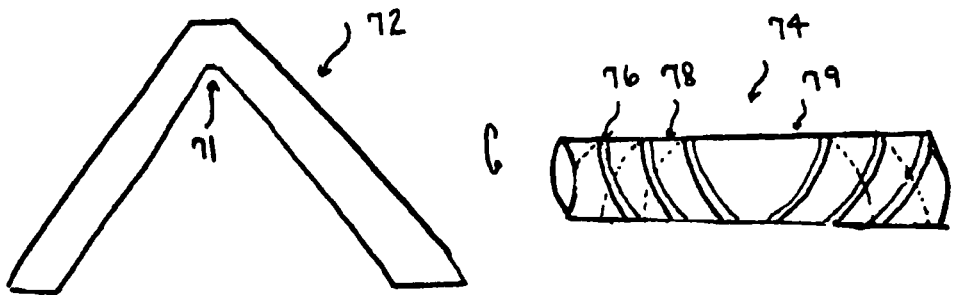
FIG. 9 illustrates a method of forming a flexible central portion according to one aspect of the invention using a material die-cut into a V-shape.
Figure 10A:
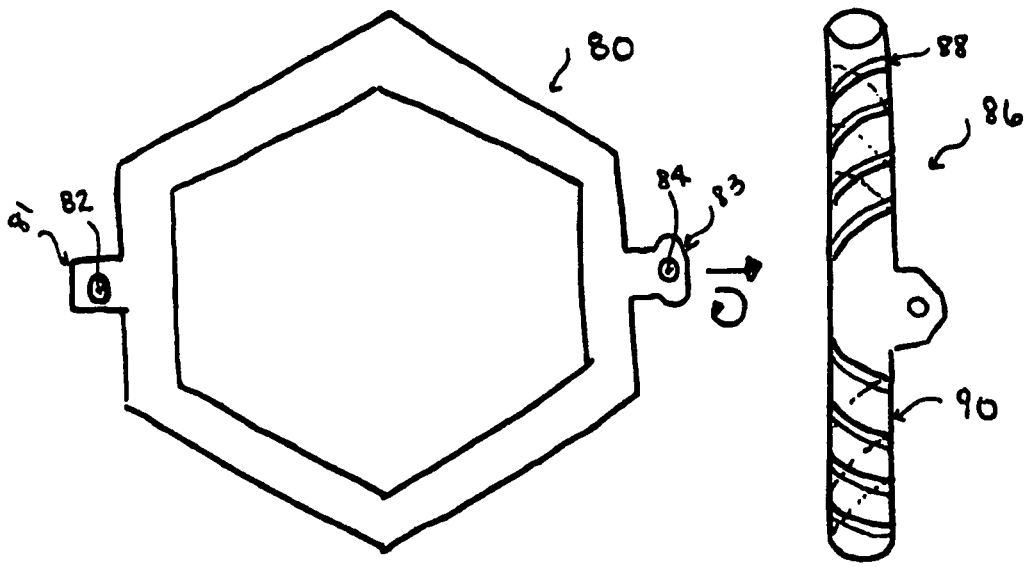
FIG. 10 illustrates a method of forming a flexible central portion according to one aspect of the invention using a material die-cut into a hexagonal shape.

In another embodiment, the flexible element is formed from a material 72 that is pre-cut into a V-shape (FIG. 9). The material 72 is wound to form a spiral pattern having slit openings 76 and solid portions 78, wherein the point of the V (71) translates into a solid segment 79 at the middle of the flexible element 74. Another variation of this concept is shown in FIG. 10A. Material 80 is pre-cut having an irregular hexagonal-shape, wherein the edges of the shape include tabs 81, 83 with eyelets 82, 84 punched therein. Once wound, a set screw inserted through the eyelets 81, 83 (now adjacent each other) may tighten or loosen the spiral pattern in the flexible element 90.

Figure 10B:
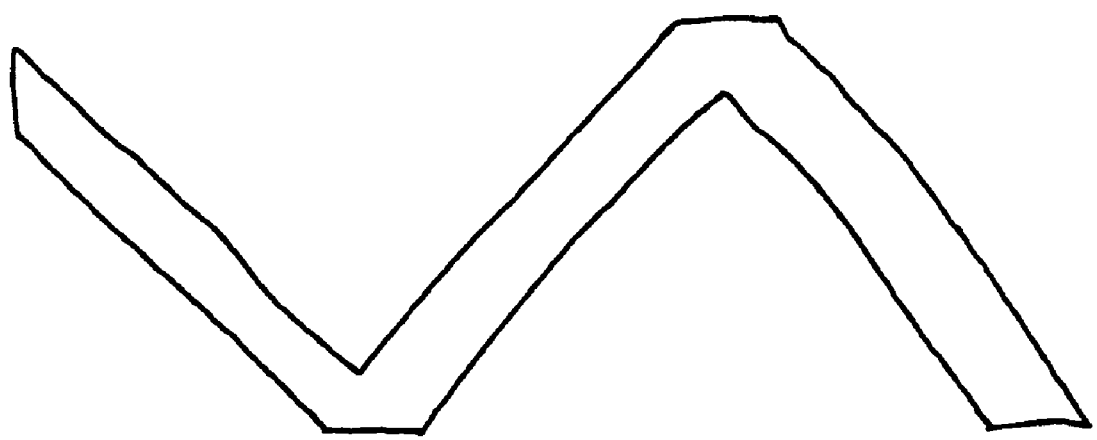
Figure 10C:
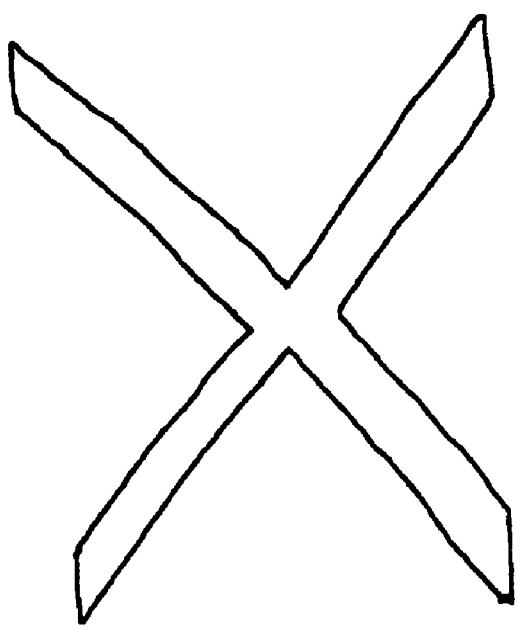
Figure 10D:
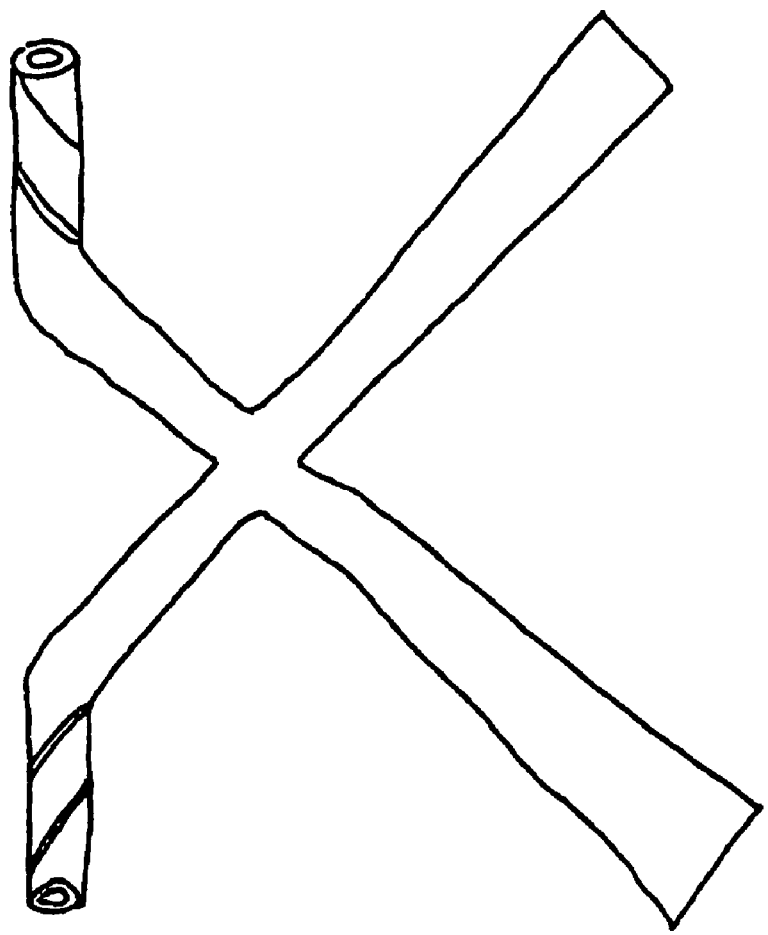
Figure 10D:
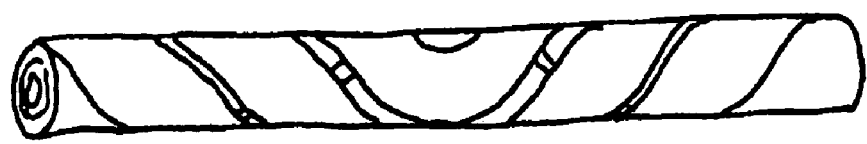

Skilled artisans would appreciate that a double walled flexible element also may be formed from additional pre-cut shapes. FIGS. 10B-D are illustrative of some of the additional pre-cut shapes that may be used to achieve a similar final construction. With regard to FIG. 10B, the flexible element is formed from a multiple V-shaped sheet. FIG. 10C shows an X-shaped sheet that can be rolled to form the flexible portion, and FIG. 10D shows that the arms of an X-shaped sheet may be tapered to provide varying thickness along the length of the flexible portion. In particular, FIG. 10D shows that the gaps or slit openings formed by the helical pattern may be larger near the center of the flexible element and become progressively smaller toward one or more ends.

In all of these embodiments where a tube is formed from a sheet of material, the sheet may be treated or coated on one or both sides to reduce friction or galling. The application of the coating or treatment preferably is performed prior to rolling the material. Additionally, an additional layer of material may be applied to the sheet prior to rolling, such as a high molecular weight polyethylene.

Figure 11A:
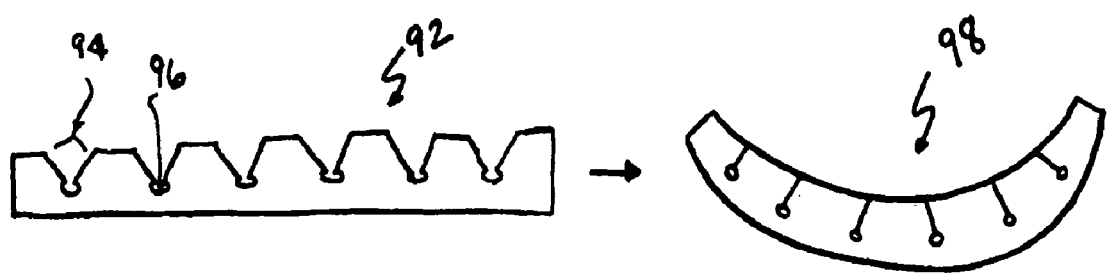
FIG. 11 is a side view of a flexible central portion having notches die-cut into the material for flexibility.
Figure 11B:
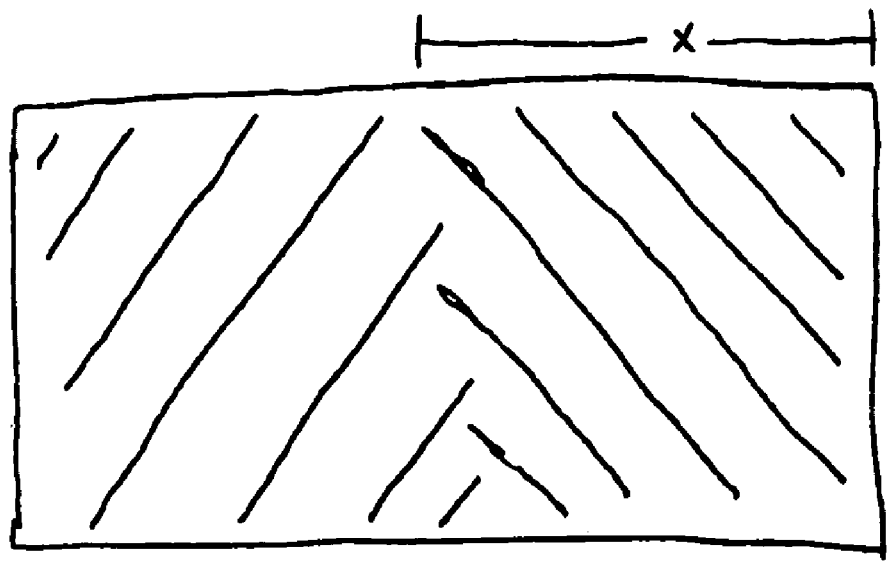
Figure 11C:
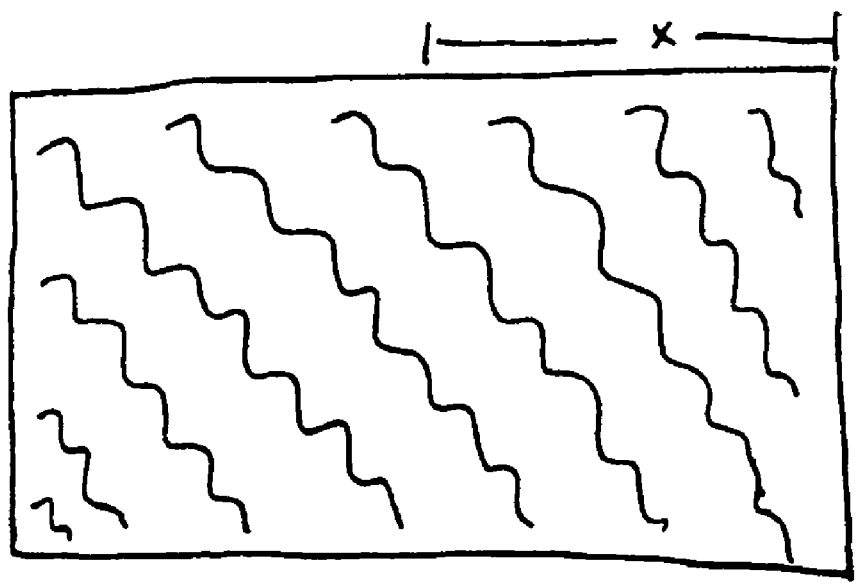

In another aspect of the invention, the flexible element may be formed from a pre-cut material 92 having notches 94 resembling a keyhole, such as shown in FIG. 11A. The tips 96 of the notches 94 may be oval in shape. When a load is applied to the material 92, the notches 94 close and the tips 96 become more circular in nature as shown in curved flexible element 98. As shown in FIG. 11B, the flexible element also may be formed from a sheet of material that is pre-cut with slits prior to forming the tube. As shown, a first plurality of diagonal slits may be formed on one side of a sheet of material and a second plurality of diagonal slits may be formed on another side of the sheet. Preferably, the first and second sets of slits are formed on a portion of the sheet that corresponds approximately to the circumference x of the tube. The slits may be straight, as shown in FIG. 11B, may have a repeating wave form as shown in FIG. 11C, or may have any other pattern of slits desired. Once the slits are formed, the sheet may then be rolled to form the tube. This process may be used to form a single wall tube or to form a tube having two or more walls as illustrated.

Figure 12:
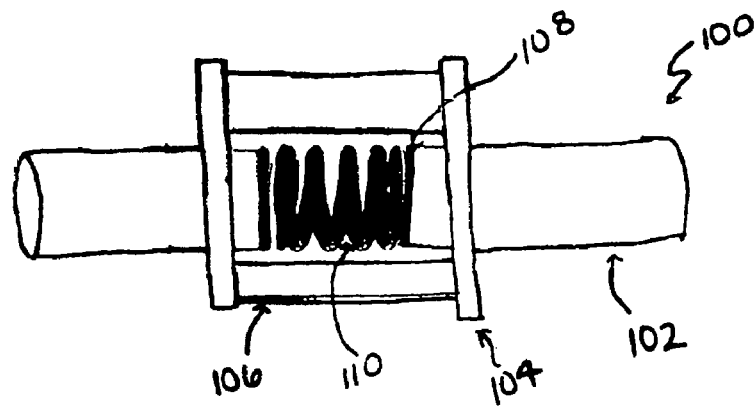
FIGS. 12 and 12A are side views of a flexible central portion according to an embodiment of the invention using a combination of solid rods and springs.
Figure 12A:
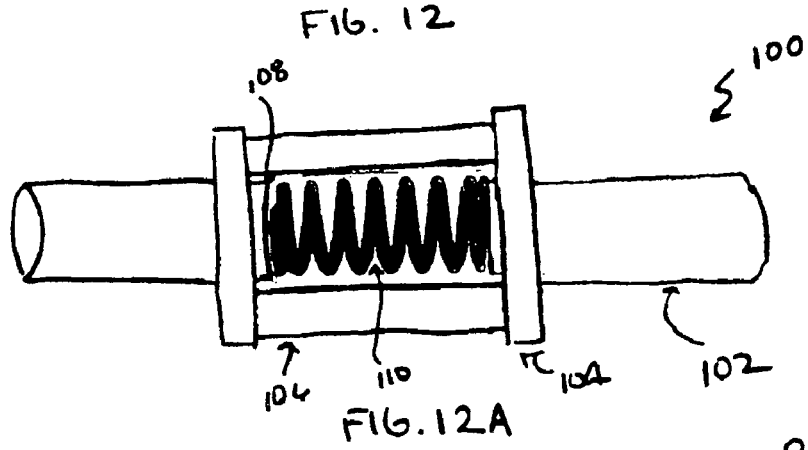

In addition, the flexible element according to the invention may be formed with an encased spring concept. For example, as shown in FIG. 12, solid rods 102 pass through a flange 104 into a tube 106. The solid rods are attached to a spring 110 via attachment means 108 or in any suitable manner. The tube 106 preferably has a diameter sufficient to allow movement of the rods 102 and attachment means 108 in response to the movement of the spring 108. In a variation of this concept (FIG. 12A, the spring 110 is longer than shown in FIG. 12 and attachment means 108 are much closer to flanges 104 than in FIG. 12, thus providing more potential flexibility to the flexible element 100. However, as those of ordinary skill in the art will appreciate, the spring constant may be varied to alter the flexibility of the flexible element 100 regardless of the length of the spring.

Figure 13:
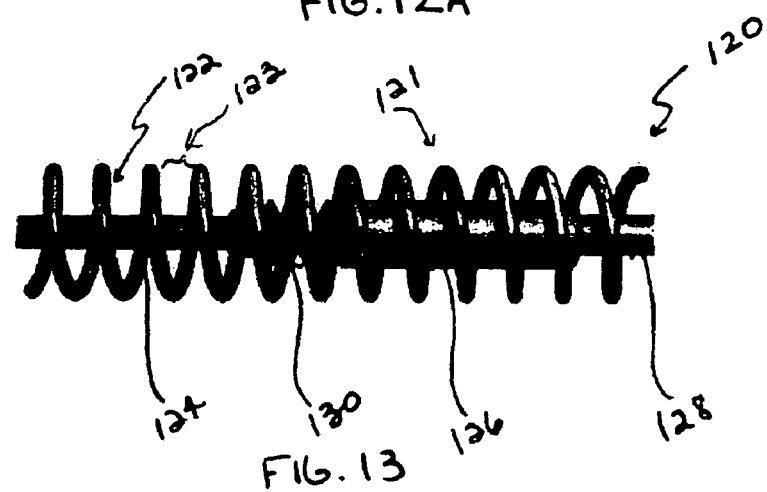
FIG. 13 is a side view of a flexible central portion incorporating a spiral pattern with a solid rod inserted therein.

In yet another embodiment, the flexible element may be formed with a solid rod within a tube having a generally helical, spiral, or thread-like pattern. As shown in FIG. 13, the outside rod 121 may be formed with much larger slit openings 123 between the solid portions 122 because a solid rod 124 is inserted into the outside tube 121 for greater stability. The solid rod 124 preferably has a diameter such that the outside tube 121 is allowed sufficient flexibility to conform to the natural movements of the motion segment unit. In one embodiment, the solid rod is formed to have different diameters along the length of the solid rod. For example, the solid rod may have segments 124, 128 having smaller diameters on the outer edges 124, 128 of the rod and a segment 126 having a larger diameter therebetween. In another embodiment, the solid rod has a flexible segment 130 somewhere along the length of the rod to allow for even greater system flexibility. This flexible segment 130 may be the result of an accordion type construction using a flexible material, a helical, spiral, or thread-like pattern cut into the solid material (similar to the outside rod), a spring-type construction, a hinge, a ball and socket joint, or the like.

Likewise, a flexible segment may be placed in a discrete portion of a solid rod as illustrated in FIGS. 13A and 13B and 26-28. As discussed above, the solid rod 134 may have a segment of flexibility 136 somewhere along its axial length that helps provide a range of motion that for the damaged or removed portion of the spine or for a portion of the spine nearby or neighboring a damaged or removed portion of the spine. Alternatively, the segment of flexibility 136 may provide only partial or limited range of motion in one or more directions as compared to the range of motion of a healthy spine.

The segment of flexibility 136 may be formed similarly to FIGS. 1 and 2 above with a spiral pattern, or it may be a separate portion to which two solid rods attach at either end. More particularly, a flexible segment 136 may be formed in a solid rod or in a single hollow tube as described above by several suitable processes, including, but not limited to, cutting one or more threads, gaps, slits or openings with a milling machine, a lathe, or by a wire EDM process. Thus, it is possible to integrally form a segment of flexibility in an otherwise solid or rigid rod.

For instance, if a wire EDM process is used, one or more holes may be drilled into the rod or tube through which a wire may be threaded. Initially, the wire EDM may cut an opening in the rod or tube in a direction that substantially corresponds to the axial length of the rod or tube. One potential benefit of providing a substantially axial cut in the rod is that it may reduce the build up of undesirable stress concentrations. The length of the axial cut may be from about 0.1 mm to about 20 mm, although more preferably it is from about 1 mm to about 10 mm. The length of the axial cut can be determined by the distance of the cut, gap, slit, or opening along the axis of the rod before it begins to wind or turn around the outer perimeter of the rod.

Eventually, the rod or tube, the wire, or both may be gradually rotated to form a generally spiral thread or opening in the material of the rod or tube. If a wire EDM cut is made along the length of the flexible segment 136, the result is that two slits or cuts are formed in the rod similar to a double helix or two-lead thread. An additional set of holes or openings also may be formed in the rod to create or start a second wire EDM cut in the rod, thereby resulting in two or more additional slits or cuts being formed in the rod. Additional cuts may be formed as well. For instance, one embodiment of the invention may involve making three or more helical, spiral, or thread-like cuts a solid rod.

Furthermore, if more than one helical, spiral, or thread-like cut is made, some of the cuts may not extend along the entire length of the flexible element. For instance, in one embodiment where the flexible element is formed from a plurality of cuts, one or more of the cuts may extend over from about 10 percent to about 80 percent of the length of the flexible element. In another embodiment, one or more of the cuts may extend over from about 20 percent to about 50 percent of the length of the flexible element.

Other techniques for forming helical, spiral, or thread-like gaps, slits or openings in a solid rod may not result in a pair of gaps, slits or openings for each cut, but instead may result in forming only one gap, slit, or threaded opening. For instance, a milling or lathe process may be used to create a single gap, slit or opening per cut. Additionally, these other processes may allow a gap, slit, or opening to be formed in the rod without cutting all the way through it. Thus, a core, inner region of a rod where a flexible element is disposed may remain solid even after gaps, slits, or openings have been formed on the outer surface of the flexible element 136. This configuration allows the solid core or inner region to resist axial compression while the outer portion allows for torsional and bending flexibility. Thus, in one embodiment the depth at which a gap, slit or opening is formed in the rod may be from about 20 percent to about 95 percent, or even 99 percent, of the radius of the rod, while in another embodiment the depth is from about 50 percent to about 80 percent of the radius or the rod.

As discussed throughout this application, there are many possible variations in the number of threads, their pitch, the gap or opening between the material that defines the thread, the material that forms the rod or tube, and the like. For example, the pitch of one or more of the helical, spiral, or thread-like cuts or slits in the flexible element formed in a solid rod may be varied in one or more portions or regions of the flexible element. Likewise, the width of the gaps, openings, or slits may be varied either along the axial length of the flexible element 136 or in a circumferential direction or side of the rod to provide greater range of motion in one direction than in another direction. Likewise, a central or mid-portion or region of flexible element 136 may have wide gaps, openings or slits than one or both ends of the flexible element 136. Without being bound to any particular theory, it is believed that providing a central or mid-portion with wider cuts, gaps, or openings may promote more bending or flexure for a given amount of permitted axial compression. Conversely, it is believed that providing a wider cut, opening, or gap at one or more ends of the flexible element may promote or permit more axial compression for a given amount of permitted bending.

The width of the gap, slit, or opening also may be varied in the circumferential direction along the surface of the flexible element 136. As described above, this configuration may permit a greater range of motion in one direction than in another. In one embodiment, the width of the gap, slit or opening may vary by about 10 percent or more, or event by about 20 percent or more, along one turn or rotation of the rod. The width of the gap, slit or opening may widen and/or narrow more than once in a single rotation of the rod. For example, a flexible element may be configured to have two wider regions on the lateral sides of the rod to permit a greater range of lateral bending than bending permitted in other directions.

Providing wider openings along a portion of the circumferential surface of a rod may also allow for the rod to be more easily bent in one direction during a surgical procedure. In this manner, the rod may be more easily customized or fitted by the physician to the anatomy of the patient.

The outer diameter of the flexible element need not be the same as the outer diameter of the solid portion of a rod. For instance, if it is desirable to create greater flexibility in the flexible element 136, the outer diameter of the portion of the rod where the flexible element is or will be formed may be reduced in size or diameter such as by cutting the surface with a lathe, a milling machine, or the like. Conversely, if a larger diameter flexible element is desired, an oversized rod may be selected and the regions of the rod that are to remain solid may be reduced in diameter using any number of processes including those mentioned above. In one embodiment, the outer diameter of the flexible element differs from the outer diameter of that least a part of a solid rod associated with the flexible element by about 10 percent or more, or even by about 20 percent or more. In another embodiment, the diameters may differ from about 5 percent to about 30 percent.

The outer diameter of the flexible element also may vary along its axial length to further vary or adjust the bending or torsional resistance of the flexible element. For example, the outer diameter or the flexible element may become progressively smaller from at least one end of the flexible element toward a central or mid-region. Thus the outer diameter of a flexible element may vary from about 5 percent to about 50 percent from at least one end toward a central region of the flexible element.

It is also possible to have more than one flexible element integrally formed in a solid rod, such as a solid rod having 2 or more, 3 or more, or 4 or more flexible elements. For instance, multiple flexible elements may be disposed in different locations of a rod so that more than one flexible element is disposed between locations on the rod where connecting elements (such as a transconnector, a bone screw, or the like) can be secured. In addition, the length of the rod may be capable of extending over multiple motion segment locations, such as a length capable of extending over 2 or more, 3 or more, or even 4 or more motion segments.

Figure 26:
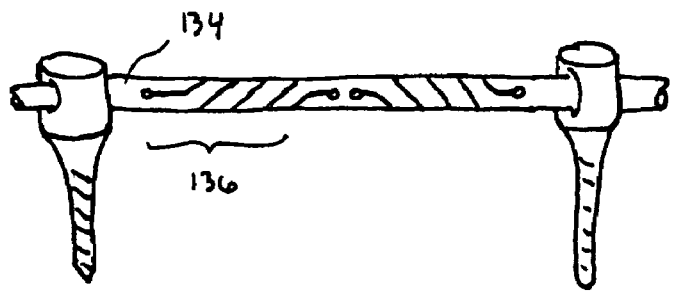
FIG. 26 illustrates a side view of the system of the invention having a plurality of flexible elements integrally formed in a rod.

If a plurality of flexible elements are formed in a single rod, the direction in which the helical, spiral or thread-like cuts travel may vary from one flexible element to another. For instance, two flexible elements in a rod may have cuts that travel in opposite directions from each other as illustrated in FIG. 26. Alternatively, the helical, spiral or thread-like cuts may travel in the same direction for each flexible element formed in the rod.

Figure 27A:
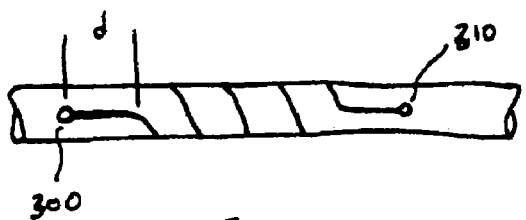
FIG. 27A is a side view of a flexible element integrally formed in a rod with starting and ending points of the flexible element in alignment.
Figure 27B:
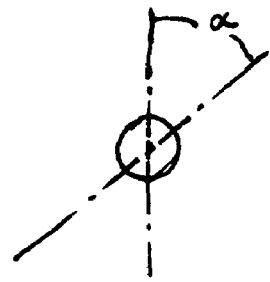
FIG. 27B is an axial view of a rod having a flexible element formed therein with starting and ending points out of alignment by a predetermined angle or amount.
Figure 28A:
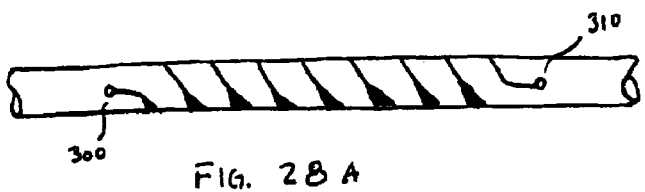
FIG. 28A is a side view of a rod having a flexible element integrally formed therein with widened cuts, slits, or openings on a portion of the perimeter of the rod.
Figure 28B:
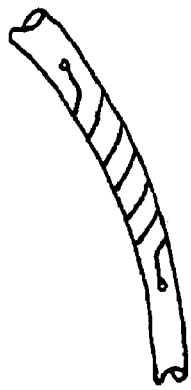
FIG. 28B is a side view of the rod of FIG. 28A while in a curved position.

As shown in FIG. 27A, one step of forming a flexible element in a solid rod may include forming a starting hole 300 and ending hole 310 in the rod. Providing a starting hole 300 and ending hole 310 in the rod may help reduce the possible occurrence of stress concentrations that could form cracks in the rod. The starting and ending holes may be aligned along the axial length of the rod as shown in FIG. 27A so that the direction of a first hole is substantially parallel to the direction of a second hole. In another embodiment, shown in FIG. 27B, the direction of the starting and ending holes may differ by an angle $\alpha$ when the directions of each hole is viewed from the longitudinal axis of the rod. For example, the angle $\alpha$ may be 30° or more. In another embodiment, the direction of the holes may differ by about 60° or more, or even may be substantially orthogonal when viewed from the axis of the rod.

Rods having flexible elements as described herein may be used in a variety of treatment methods. For instance, a flexible element formed in an otherwise solid or rigid rod may be used in fusions to optimally load bone graft in the anterior column. When used in conjunction with the fusion process, rods having flexible elements may help support 1 or more motion segments disposed adjacent to or near the fused region of the spine. Providing flexible elements in rods extending beyond the fused region of the spine to 1 or more, or 2 or more neighboring motion segments can allow these neighboring motion segments to be more stabilized without requiring more extensive fusion.

In addition, stabilization systems of the present invention may be used to aid in correcting undesired curvature of the spine. For example, the flexible element and rods may be configured or shaped to approximate the natural curvature of a healthy spine. In areas or regions where a patient's spine curvature or shape does not correspond to this natural curvature of a healthy spine, the flexible element may be deflected or bent so that the rod corresponds more closely to the patient's spinal curvature. Preferably, the bending or loading of the rod and flexible element are not significant enough to cause the rod or flexible element to permanently deform. Over time, the preloaded forces applied to the rod and flexible element may gradually urge the undesired curvature of a treated portion to more closely resemble the curvature of a healthy spine.

Figure 14:
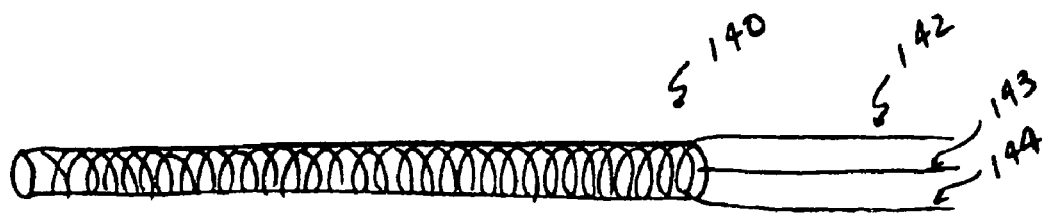
FIG. 14 is a side view of a braided flexible central portion according to an embodiment of the invention.
Figure 13A:
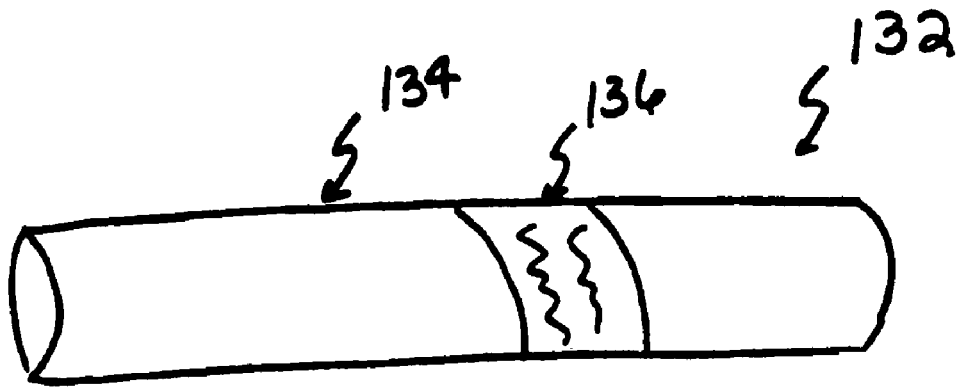
FIGS. 13A-B are side views of flexible central portions according to the invention incorporating a flexible segment between two solid portions.
Figure 13B:
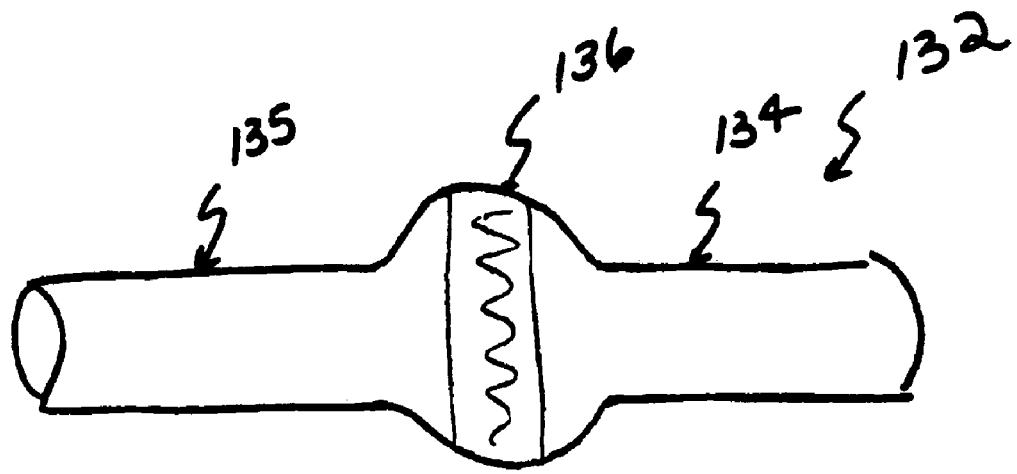

The flexible element may also be formed using a braided wire. FIG. 14 illustrates three strands of material 142, 143, and 144 braided together to form a flexible central portion 140. The strands 142, 143, 144 may be formed from identical materials or may differ from each other. For example, strand 142 may be wire, whereas pieces 143 and 144 may be rubber-based. In one embodiment, a solid rod (not shown) can be inserted into the braided flexible central portion. In another embodiment, the solid rod is present while the material 142, 143, and 144 are braided. While FIG. 14 shows only three strands of material, this aspect of the invention encompasses multiple pieces braided with each other, as well as less than three strands braided together.

Figure 15:
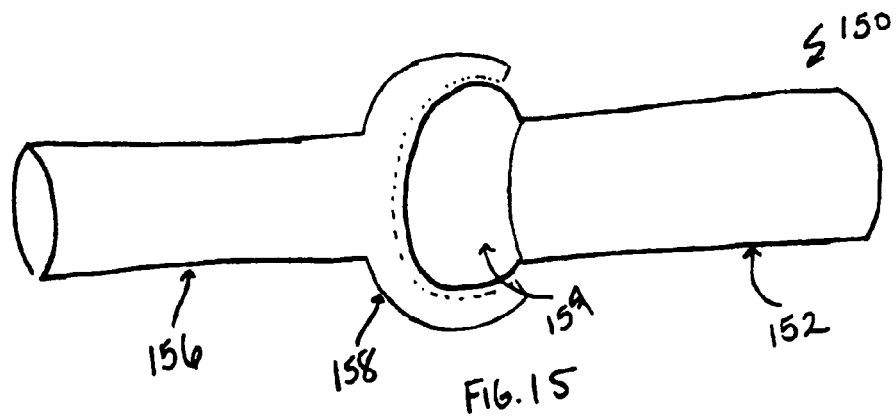
FIGS. 15 and 15A are side and perspective views of a flexible central portion incorporating a ball and socket joint for flexibility.
Figure 15A:
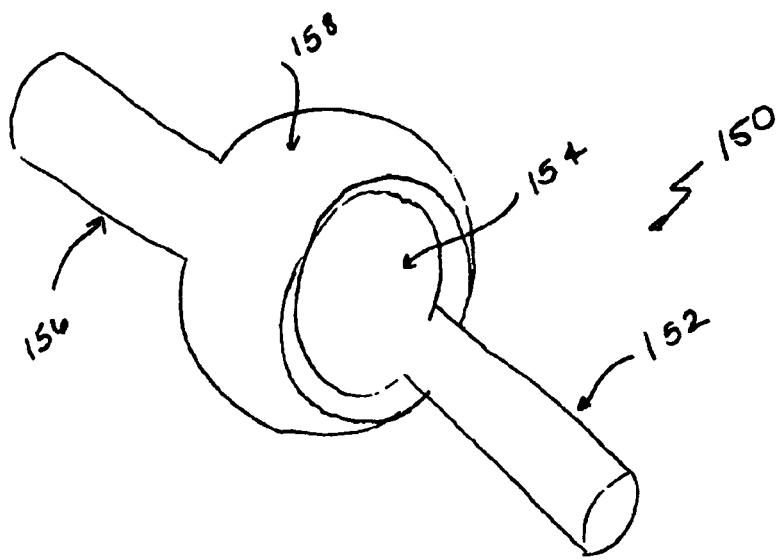
Figure 16:
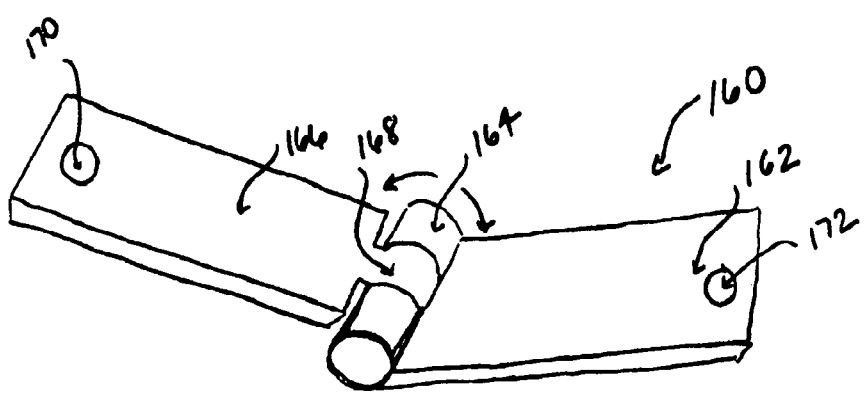
FIG. 16 is a top view of a flexible central portion according to the invention incorporating a hinge for flexibility.

In another aspect of the invention, the flexible central portion may be formed using a joint concept. For example, FIGS. 15 and 15A show a flexible central portion constructed having a ball and socket joint to enable flexibility. The flexible central portion 150 includes a first solid rod 152 having a ball 154 at the end and a second solid rod 166 having a socket 158 formed to fit the ball 154. The ball and socket joint allows rotational movement of the flexible central portion 150 so that the overall system may respond to spinal movements in a more natural fashion. Likewise, FIG. 16 illustrates a flexible central portion 160 having a hinge for flexibility. The flexible central portion 160 includes a first wing 162 having a collar 164 and a second wing 166 having a pin 168. The pin 168 and collar 164 allow for lateral movement, but not rotational movement.

The flexible element may be made from a variety of materials. For example, flexible element may be made of any metal appropriate for surgical implantation, such as stainless steel, titanium, titanium alloy, chrome alloys. In one embodiment, the flexible element of the system may be fashioned out of shape memory materials or alloys, such as nickel titanium. In addition, the flexible element may be formed from non-metallic materials including, but not limited to, carbon fiber, resin materials, plastics, and ceramics. In one embodiment, the rod portion is formed from a bioresorbable material. In another embodiment, non-bioresorbable materials including silicone, polyurethane, polyester, polyether, polyalkene, polyamide, poly(vinyl) fluoride, polytetrafluoroethylene (PTFE), silk, glass, carbon fiber, and mixtures thereof may be used to form any part of the flexible element. In addition, composite materials, such as a matrix of fibers, may be used to form at least a part of the flexible element.

As known to those of ordinary skill in the art, the selection of materials has a host of effects on the performance of the formed flexible element. For example, the flexural rigidity, modulus of elasticity (i.e., degree to which a material deforms as a result of a given stress), and thickness of the selected material will effect the amount of deflection (i.e., the relative stiffness of the flexible central portion), flexural modulus, torsional rigidity of the flexible element. A flexible element made from metal will have a higher flexural rigidity than the same flexible element made from a rubber-based material.

It is also known, however, that the material selection is only one way to control the properties of the flexible element. The properties may likewise be controlled, at least in part, by adjusting the degree of curvature of the flexible element. For example, the amount of deflection is directly related to the amount of strain energy, which is, in turn, directly related to the degree of curvature of the flexible element and inversely related to the modulus and thickness of the material. Therefore, the characteristics of the flexible element are dependent on the modulus of elasticity, material thickness, radius of curvature, and arc of curvature. For example, by decreasing the radius of curvature and increasing the arc measure and holding all other parameters constant, more flexibility (less stiffness) may be imparted to the flexible central portion and the amount of deflection may also be increased. In addition, altering the modulus of elasticity and holding material thickness, radius of curvature, and arc of curvature constant, the relative stiffness any part of the flexible element may be adjusted.

Bone Fasteners

The bone fasteners included in the system of the invention include any type of fastener that may be attached to the flexible central portion of the invention, while remaining securely fastened onto the intended bone. Thus, the bone fasteners may include polyaxial screws, helical blades, expandable screws, such as Mollie bolt type fasteners, which are inserted or screwed into the bone and expand by way of some type of expansion mechanism, conventional screws, staples, sublaminar hooks, and the like. In one embodiment, the bone fasteners are coated with any number of suitable osteoinductive or osteoconductive materials to enhance fixation in the bone. In another embodiment, the bone fasteners are fenestrated to enhance bony ingrowth or to further anchor the fastener to the bone.

Figure 17:
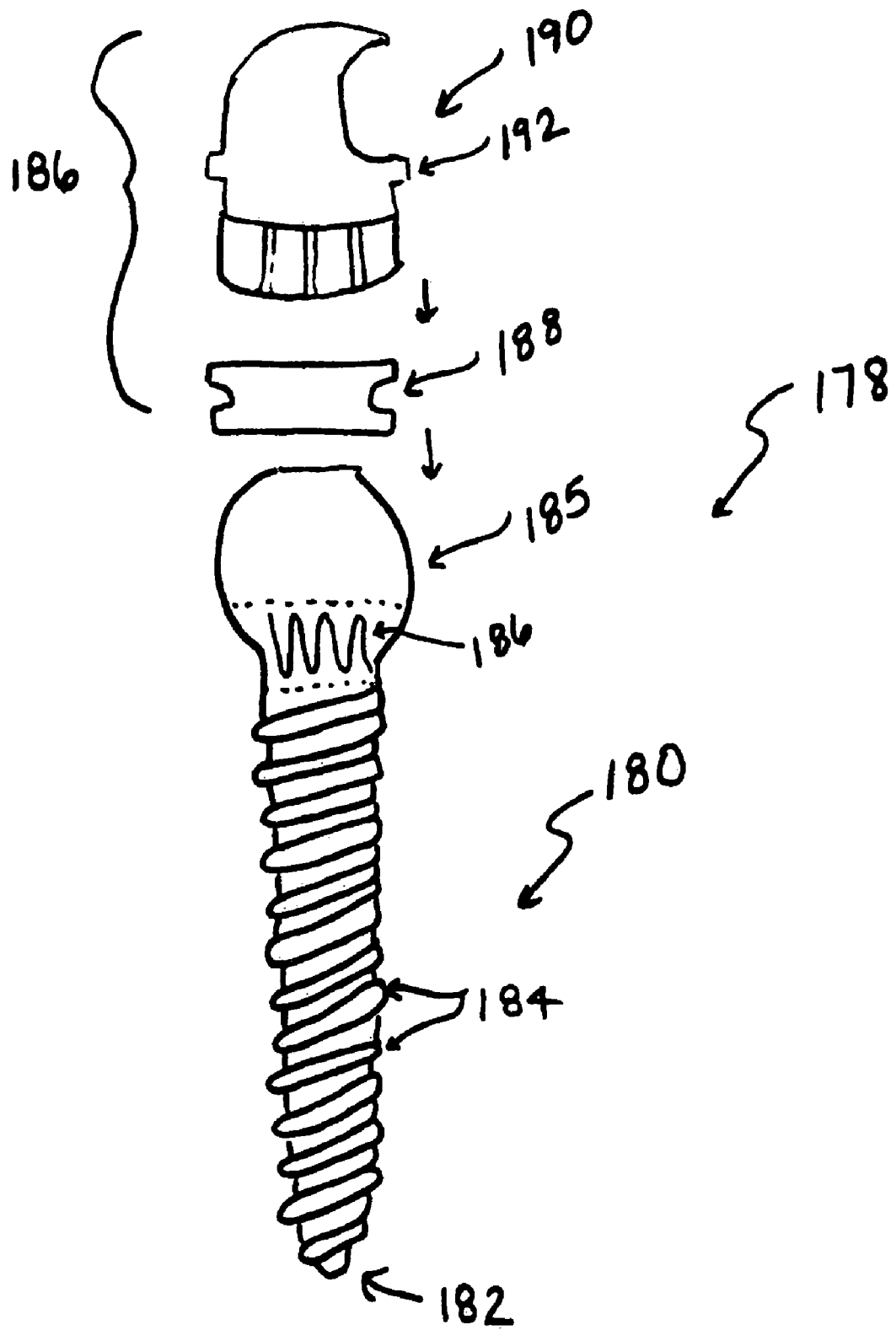
FIGS. 17-20 are frontal views of bone fasteners according to various embodiments of the invention.

In one embodiment, the bone fasteners are polyaxial screws, such as the one shown in FIG. 17. The polyaxial screws preferably include a linear middle segment 180 with a tapered tip and a plurality of protrusions 184, which defines the insertion segment of the fastener 180, and a receiving segment 186. The receiving segment may be a separate, attachable unit to be added after the fastener is inserted into the bone.

The insertion segment preferably has a tapered tip 182 for easier insertion into the bone. In one embodiment, the tapered tip defines an angle of 60° or less, preferably about 45° or less. The plurality of protrusions 184 extend laterally from the linear middle segment 180. The at least one protrusion preferably has a leading edge designed to follow the general design of the tapered tip 182 of the insertion segment 180. In one embodiment, the leading edge defines an angle of 60° or less, preferably about 45° or less. Thus, the leading edge does not prevent insertion of the bone fastener into the bone, but instead provides a secure fit once into the bone and prevents the bone fastener from loosening its way out of the bone over a period of time. The height of each protrusion greatly depends on the number of protrusions present on the linear middle segment 180. One of ordinary skill in the art would be aware of how to select the number, angle, and height of the protrusions so as to provide optimal bone fastening.

Figure 18:
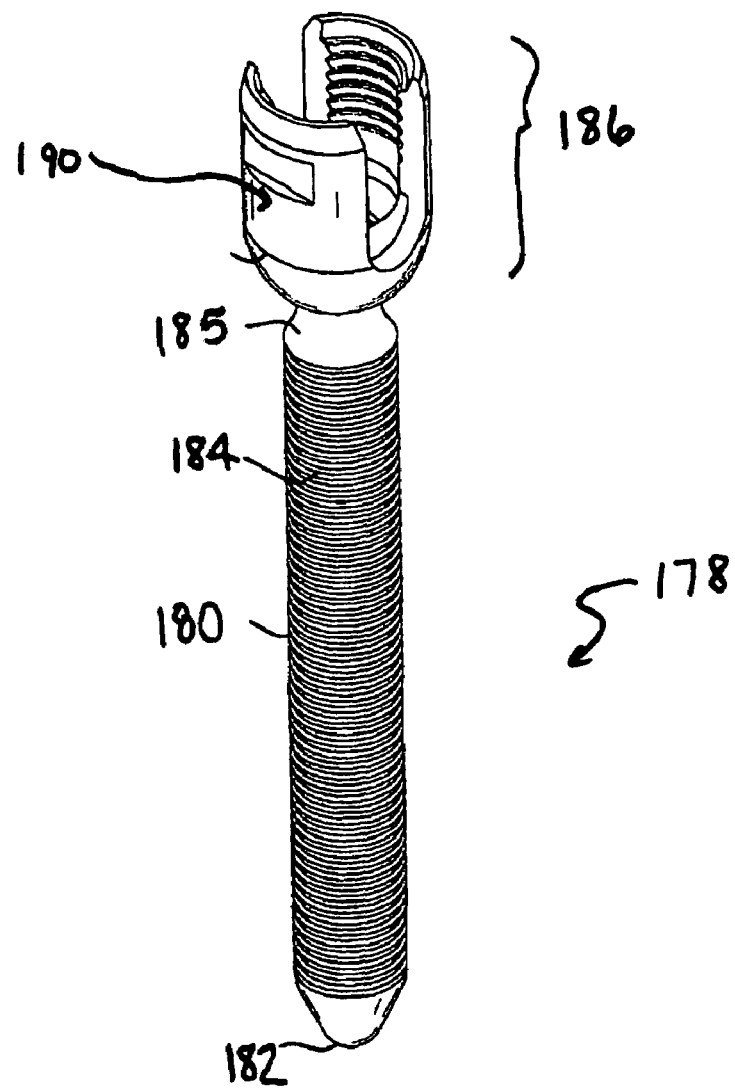

The receiving segment 186 of the bone fastener 178 may be fashioned in a number of ways, all of which preferably involve providing the receiving segment the ability to accept the flexible central portion of the system. For example, the receiving segment may be designed to be top loading, side loading, eye-hole loading, and the like. FIG. 17 illustrates a receiving segment having a collar 188 and a side-loading head 190. Once inserted into the bone, the collar may be placed over the top 185 of the insertion segment 180. A tool may then be used to push the locking bar 192 of the head 190 down over the collar. FIG. 18 shows a top-loading head 190 that is already locked down into place over insertion segment top 185.

Figure 19:
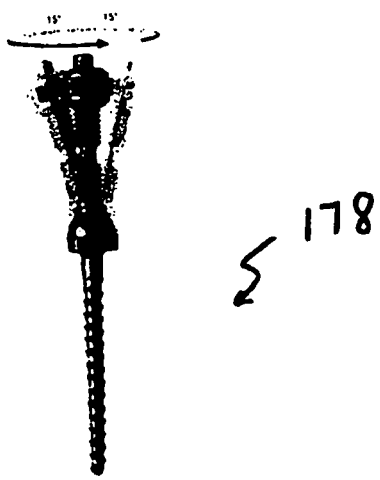
Figure 20:
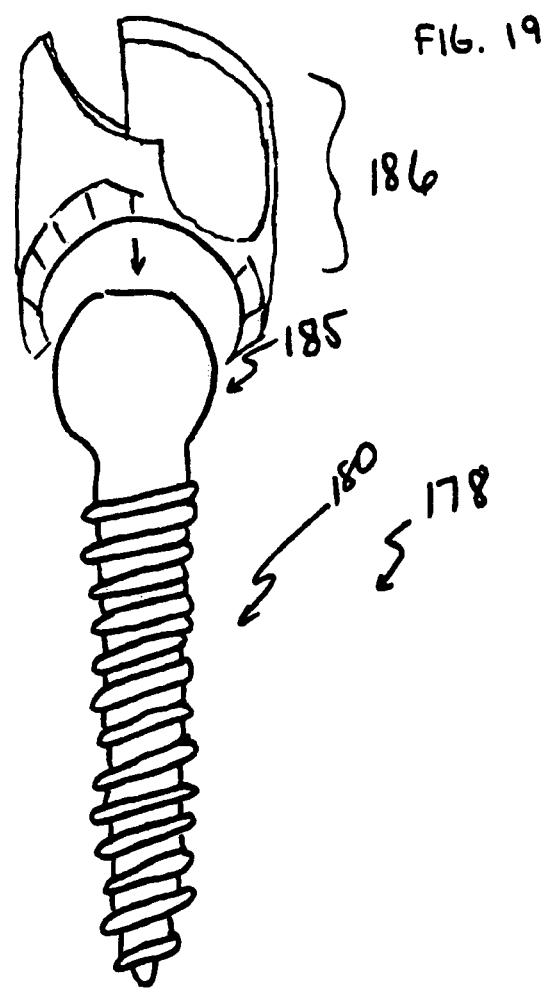
Figure 21:
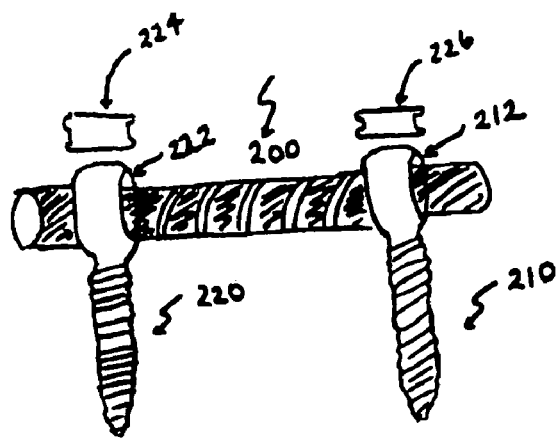
FIGS. 21-23 are side views of the assembled system of the invention according to various embodiments discussed herein.

The bone fastener may be designed to have rotational capabilities. In one embodiment, the bone fastener has at least about 10 degrees of rotational freedom. In one embodiment, the bone fastener has at least about 20 degrees of rotational freedom. In still another embodiment, as shown in FIG. 19, the bone fastener has about 30 degrees or freedom or greater. In yet another embodiment, the bone fastener has about 45 degrees of freedom or greater. In this aspect of the invention, the freedom of the receiving segment may be accomplished in a variety of ways. For example, the insertion segment 180 and receiving 186 segment may function like a ball and socket joint (as shown in FIG. 20), where the rotation mechanism of the joint allows articulation within some spherical range of motion. The top 185 of the insertion segment 180 functions as the "ball" and the receiving segment 186 functions as the "socket". In addition, a flexible segment is incorporated into the bone fastener (as depicted by the dashed segment near the top 185 of insertion segment 18 in FIG. 17).

The bone fasteners may be made from a host of materials. For example, the fasteners may be formed from natural/biological materials, such as allograft, xenograft, and cortical bone. The fasteners may also be formed from synthetic bioresorbable materials, such as polyanhydride, polyactide, polyglycolide, polyorthoester, polyphosphazene, calcium phosphate, hydroxyapatite, bioactive glass, tyrosine-derived polycabonate, and mixtures thereof. In another embodiment, the fasteners are formed from non-bioresorbable materials including, but not limited to, stainless steel, titanium, titanium alloys, cobalt chrome alloys, shape-memory alloys, and carbon-reinforced polymer composites.

In addition, the fasteners may include growth factors for bone ingrowth and bony attachment, or for soft tissue ingrowth. Non-limiting examples of growth factors include insulin-like growth factor 1, basic fibroblast growth factor, transforming growth factor β-1, platelet-derived growth factor, bone-derived growth factors, arginine, bone morphogenetic protein, LIM mineralization protein, and combinations thereof.

As mentioned previously, the flexible element also may be used in other component of a spinal fixation system. For instance, it may be used as part of a transconnector. In this embodiment, the flexible element may be disposed between two fasteners connected to rods positioned along the length of the spine. Any fastener that may be suitable for a conventional transconnector may be used with the present invention. Some examples of fasteners are described in U.S. Pat. No. 6,565,565 to Yuan, U.S. Pat. No. 6,562,040 to Wagner, U.S. Pat. No. 6,551,318 to Stahurski, and U.S. Pat. No. 6,540,749 to Schafer, all of which are incorporated herein in their entireties.

Assembly of the System

The flexible element may be connected to fasteners in a number of ways, i.e., so that the connection is constrained, unconstrained, articulated, or combinations thereof. For example, when the receiving segment is fixed onto the insertion segment via a locking bar over a collar, such as shown in FIG. 17, the flexible element may be constrained or rigidly fixed within the receiving element of the insertion segment. In one embodiment, the flexible element 200 would be flexible only between the two bone fasteners 210 and 220. The flexible element may be inserted into heads 212 and 222, which can be side-loading or top-loading in this aspect of the invention. Following the placement of the flexible element within the heads 212 and 222, clamping screws 224 and 226 are inserted into the heads and firmly screwed down securing all the connected elements in place. This design would allow flexibility between the two bone fasteners only.

In another embodiment, the flexible element 200 is not fixed to the heads 212 and 222 of the bone fasteners 210 and 220, but instead is able to slide longitudinally within the heads 212 and 222. This may be accomplished using heads with eyeholes, as discussed above. In such an embodiment, it is preferable that the heads and/or flexible element have means for limiting the slidability so that the flexible element does not move completely though the eyehole. Pins or bars may be sufficient to accomplish this "stop" mechanism. Thus, in this embodiment, the flexible element would be able to flex between the bone fasteners and also shift longitudinally within the receiving elements.

Using bone fasteners with rotational capability, as discussed above with reference to FIGS. 17, 19 and 20, may be used to obtain flexibility for the system of the invention. In such an embodiment, the system of the invention may include a solid rod 230 inserted into the side-loading, top-loading, or eyehole loading heads 242 and 252 of the bone fasteners 240 and 250. A flexible fastener element 244, 254 in each of the bone fasteners 240 and 250 allows a specific range of motion defined by each bone fasteners degrees of freedom. As discussed above, this general concept may also be accomplished using bone fasteners having ball and socket joint fittings as shown in FIG. 20.

Figure 22:
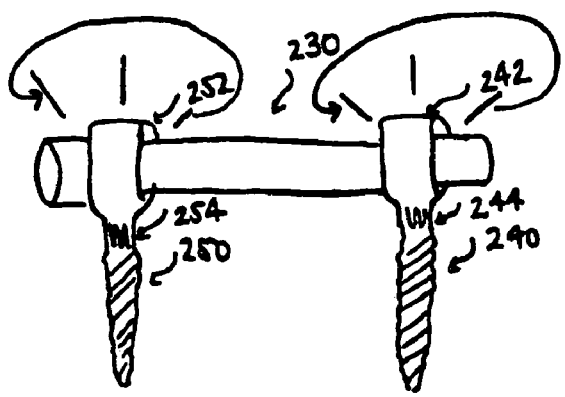

In this aspect of the invention, the bone fasteners 240 and 250 have about 10 degrees or greater degrees of freedom. In another embodiment, the bone fastener has at least about 20 degrees of freedom. In still another embodiment, the bone fastener has about 30 degrees or freedom or greater. In yet another embodiment, the bone fastener has about 45 degrees of freedom or greater. While a solid rod is depicted in FIG. 22, it is contemplated that bone fasteners having flexible fastener elements may also be used with any of the embodiments described herein. In fact, using bone fasteners with rotational capability in combination with a flexible element may impart both flexibility though axis rotation of the flexible element and the bone fastener, as well through bending capability.

Figure 23:
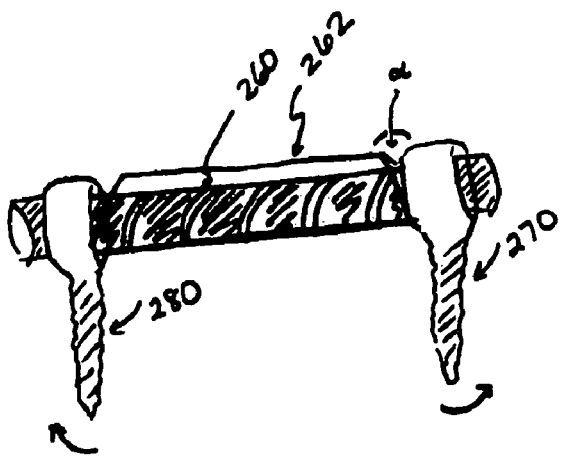

Another way to impart motion capability to the system of the invention is illustrated in FIG. 23. The flexible element 260 is encased within a solid tube 262. The solid tube 262 preferably has a diameter large enough to allow the flexible central portion 260 to bend laterally and longitudinally in response to the natural spinal movement. The bone fasteners 270 and 280 also impart some motion to the system, although the motion is limited by the angle α between the solid tube 262 and the bone fasteners 270 and 280.

Figure 23A:
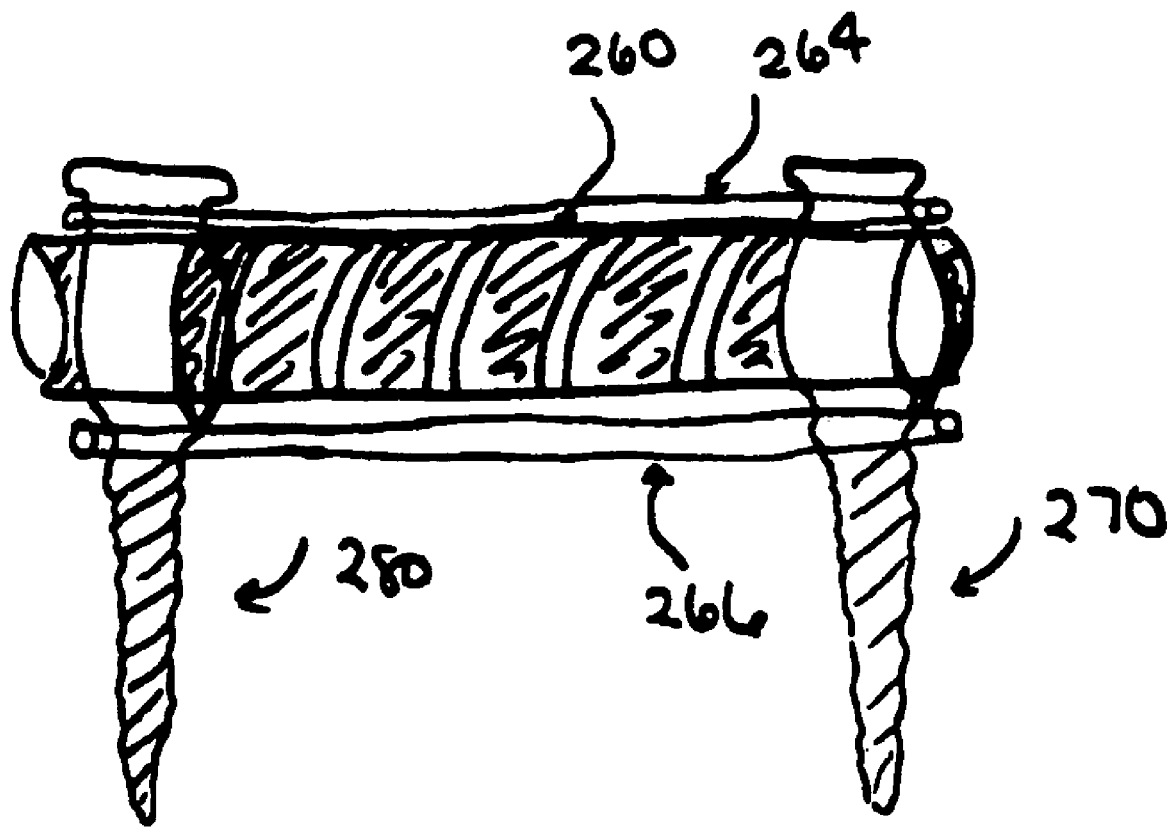
FIG. 23A is a side view of an assembled system of the invention using tension bands in addition to the flexible central portion.

Another variation on the construction of the system includes one with tension bands on both sides of the flexible central portion, as shown in FIG. 23A. This system includes a flexible central portion 260, bone fasteners 270 and 280 securing the bone fasteners 270 and 280, and two tension bands 264 and 266. The tension bands may be made with a variety of materials, such as wire cables, flexible plastics, rubber-based materials, among others having the properties needed to provide tension capability to the system. The flexible central portion 260 acts a shock absorber in compression of the motion segment unit and restores the natural height of the unit and the tension bands 264 and 266 act to limit the amount of tension in the unit. When a tension force is applied, the tension bands 264 and 266 become taught through flexion or extension. One or more tension bands also may be disposed within a hollow flexible element such as a tube, a plurality of tubes, or in several of the other embodiments.

In still another embodiment, the system may use the flexible element depicted in FIGS. 3A-B, wherein the flexible central portion is loaded onto the bone fasteners before the heads of the bone fasteners are connected. The eyelets in the ends of the flexible central portion shown in FIGS. 3A-B may be concave in order to receive another identical concave eyelet to reduce shearing. In such a design, the heads of the bone fasteners may be fixed or have rotational capability depending on the flexibility desired of the system.

Figure 24:
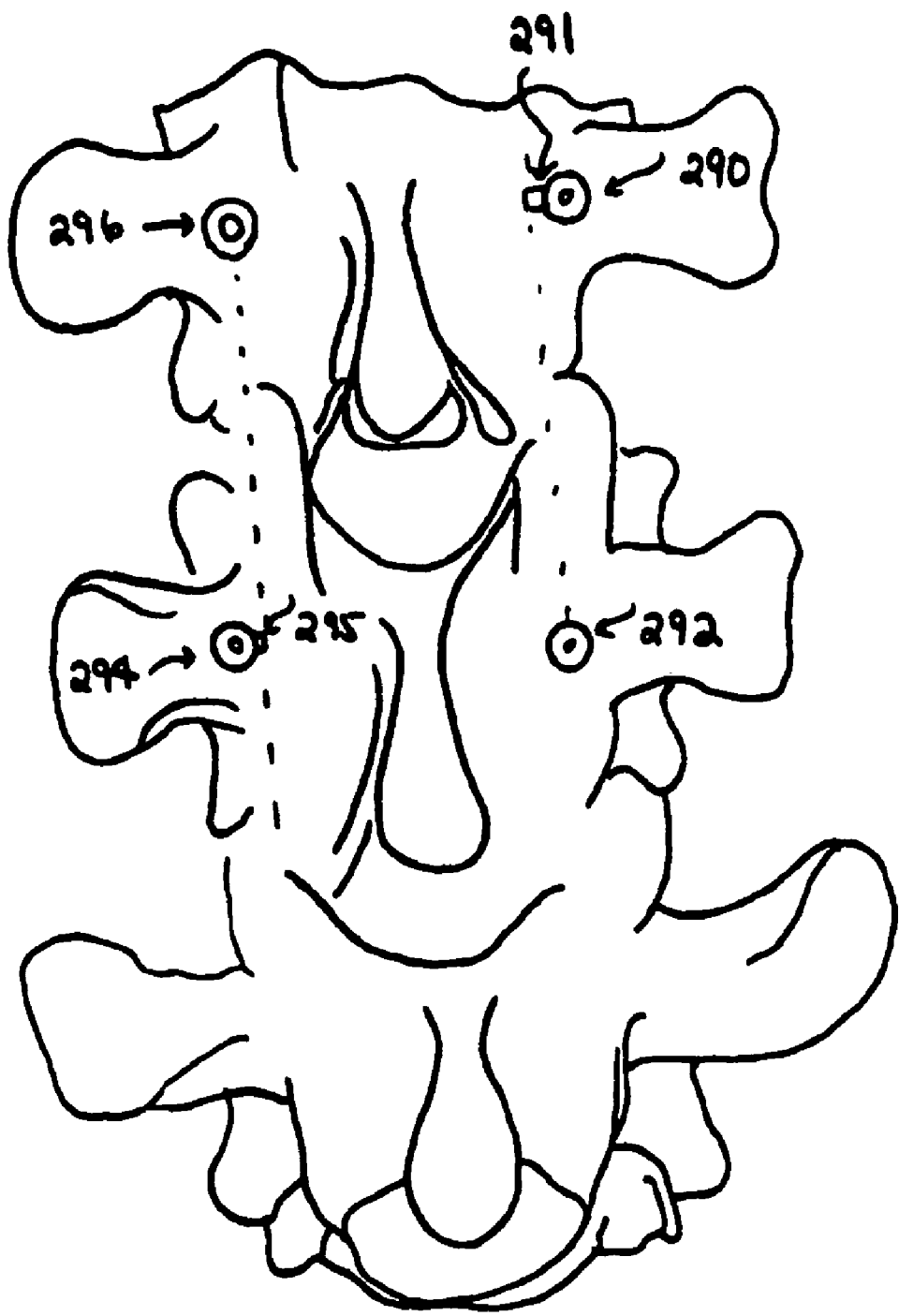
FIG. 24 is a frontal view of a motion segment unit with bone fasteners driven therein.

In addition, adjustable connectors may be used to correct any non-linear patterns of the bone fasteners once inserted into the bone. For example, because of the curvilinear nature of the spine, the bone fasteners may not line up vertically. FIG. 24 shows bone fasteners 290, 292, 294, and 296 connected to the bone, wherein the bone fasteners 290 and 292 and bone fasteners 294 and 296 do not line up vertically with respect to each other. Thus, to connect the flexible element to the pedicle screws, at least one adjustable connector 291, 295 may be used to compensate for this non-linear pattern. The adjustable connector may be rigid or flexible in nature depending on the desired stiffness of the system.

The stiffness of the system of the invention may also be adjusted during the operation and post-operation using a set screw. This would allow surgeons and doctors to make adjustments depending on a specific scenario.

Figure 25:
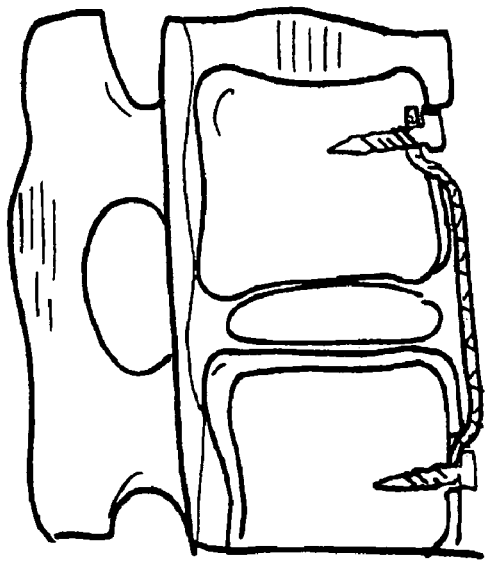
FIG. 25 illustrates a side view of the system of invention as implanted within a motion segment unit.

The system, once assembled, may serve a variety of functions in the motion segment unit (FIG. 25). For example, the system may reduce the load on the degenerative disc and/or facet joints in the motion segment unit. In addition, the height of the adjacent vertebrae may be restored to eliminate crushing or slipping of the disc therebetween. Moreover, lordosis may be created/preserved using the system of the invention in at least one motion segment unit of the spine. Furthermore, the stiffness of the motion segment unit may be restored with the implementation of the system of the invention.

In some embodiments, rods having flexible elements formed therein may be disposed in combination with rods used to make a portion of the system rigid. For example, a motion segment neighboring a treated area that has been essentially immobilized with a rigid stabilization system may be supported with a flexible element. Some examples of how a flexible element may be utilized in this manner, or even independently of a rigid stabilization system, are illustrated in FIGS. 30A and 30B. For instance, FIG. 30A shows that a flexible element may be disposed generally between the locations of bone screws used to secure the system to the spine. For instance, the flexible element may be disposed in the posterior region of the spine where the spinous process is located. The bony anatomy of all or part of the spinous process may be removed in locations where the flexible element will be placed. In this position, the flexible element may provide axial support of the spine with minimal moment forces, bending, or cantilever loading from axial compression. This configuration also may permit the flexible element to bend or flex both laterally and from front to back, thereby providing a wide range of motion that can be customized in any of the ways described herein.

For instance, the flexible element may limit or allow motion in different planes, such as a wide range of motion for flexion/extension but a smaller range for lateral bending. One way this can be achieved is by varying the width or size or the opening, cut, slit, or gap along the outer perimeter of the rod, as shown in FIG. 31B. Varying the size of the opening, cut, slit, or gap allows the range of motion for different planes to be selected and controlled independently of each other. For example, lateral bending may be limited to ±10°, ±2°, or fully restricted (±0°) without affecting the range of motion available for flexion/extension. Likewise, flexion/extension may be provided for ±30° of motion, ±20° of motion, ±5° of motion, or fully restricted.

As shown in FIG. 30B, two or more flexible elements may be utilized for a motion segment. One advantage of this configuration is that the flexible elements may continue to permit bending by flexion/extension while providing greater resistance to lateral bending. Providing two flexible elements with rigid transconnectors as shown in FIG. 30B provides greater structural resistance to lateral bending because one flexible element may have to increase in length while the opposing one would need to compress or shorten in length during lateral bending.

In general, the threads, slit, cut or openings described above use a center or centroid of the cross-sectional profile of the rod as the center of the threads, slits, cuts or openings. In other words, the center of a circular rod may be used as the center of the curvature of the threads, cuts, slits, or openings formed on the rod. This configuration is shown in FIG. 32A. Thus, a wire EDM cut may originate by forming a hole that passes through the center of the rod and then rotating and translating either the rod, the wire, or both, to form a cut or opening. In this manner, the radius of the cuts, slits, or openings are the same as the radius of the rod.

This configuration, however, need not be applied in every embodiment of the invention, however. For example, as shown in FIG. 32B, the rotational axis of the wire EDM (or of any other cutting device) may not be disposed at the center or centroid of the cross-sectional area of the rod. By manufacturing the thread, cut, slit, gap or opening so that it is not on center, it may be possible to provide one relatively stiff, main load bearing portion of the flexible element and a "back-up" or binding element that could constrain the ends in the event the load bearing portion failed.

In another embodiment, all or a portion of the voids of the gaps, threads, cuts, slits or openings may be filled with elastomer, a material that may be absorbed by the body over time (e.g., the flexible element is initially rigid, but gradually becomes more flexible as the patient recovers from surgery), a medication (such as bone growth or chemotherapeutic substances), or the like. The inclusion of material in the voids of the gaps, threads, cuts, slits, or openings may be provided on only a portion of the axial length of the flexible element, may be provided in only a portion of the perimeter of the flexible element, or both.

As mentioned above, one or more flexible elements may be provided in a transconnector, a rod, in a bone screw or other fastener, or in any other component where controlled flexibility is desired.

Kits

Revisions to the spine or motion segment units therein bring uncertainty to the surgeons performing the operations. The original diagnosis may be altered once the motion segment unit is decompressed. Required instruments are sometimes not known until the procedure is under way and the original diagnosis may be altered or augmented. Thus, the present invention also contemplates kits including various flexible segment portions, rigid rods, and various bone fasteners, as well as the tools needed for surgery. The kits of the invention are intended to broaden a surgeon's options once in surgery to provide a patient with the most optimal spine stabilization system. By containing the most common instrument needs and options for assembling the actual spine stabilization of the invention, the revisions are completed faster and with fewer sets from central supply. Overall, there is less of a labor burden on hospital staff and procedure time is reduced by having all required instruments in one convenient kit.

An example kit may include two of each flexible elements depicted in FIGS. 1-4, 11, and 12-16, two rigid rods, six of each of the bone fasteners depicted in FIGS. 17-20, cutters, an awl, forceps, screwdriver, probe, and at least one locking tool adaptable for use with the bone fasteners.

Bone fasteners may be manufactured in varying widths and lengths and the flexible element may also come in various lengths. Thus, bone fastener cutters and cutters for the flexible element are included within the kit to cut the selected parts of the system to any desired size. For example, if the flexible element is a braided wire, simple wire cutters may be used to cut the flexible element to the desired size. Also, to cut the unneeded part of the bone fastener, manual screw cutters and gas-powered screw cutters are contemplated for use with the present invention.

Additionally, the present invention may be used to form other component that may be included in a kit. For example, the present invention may be used to form a transconnector between two rods. When used with a transconnector, it is preferred that the present invention is capable of becoming rigid once it is in a desired position. For example, the surgeon is able to flex or more portions of the transconnector around bony anatomy. Once it is in a desired position, the flexible portion may then be made rigid so that the rod resists flexural and torsional forces. As mentioned previously, examples of transconnector designs that may be improved by the present invention are described in U.S. Pat. No. 5,743,911 to Cotrel, U.S. Pat. No. 5,651,789 to Cotrel, U.S. Pat. No. 6,139,548 to Errico, U.S. Pat. No. 6,306,137 to Troxell, U.S. Pat. No. 5,947,966 to Drewry, U.S. Pat. No. 5,642,442 to Mellinger, and U.S. Pat. No. 6,524,310 to Lombardo, all of which are incorporated herein in their entireties.

While it is apparent that the invention disclosed herein is well calculated to fulfill the objects stated above, it will be appreciated that numerous modifications and embodiments may be devised by those skilled in the art. Therefore, it is intended that the appended claims cover all such modifications and embodiments that fall within the true spirit and scope of the present invention.

What is claimed is:

1. A flexible spine stabilization system comprising:
   a rod having a substantially solid body extending from a first end portion to a second end portion, the rod made from a first material;
   a first flexible element formed in the body of the rod comprising at least a first slit formed on the body of the rod, wherein said first flexible element is disposed between the first and second end portions, wherein the first flexible element is integrally fonned between said first and second end portions,
   wherein a second material is positioned within at least a portion of the slit, the second material being bioabsorbable, and
   wherein the first flexible element has a first flexibility that permits motion of the first end portion relative to the second end portion and the first flexibility increases over time as the second material is absorbed;
   a first fastener connected with the first end portion; and
   a second fastener connected with the second end portion;
   wherein the first and second fasteners are adapted to secure the rod at least partially between the exterior of a first vertebra and a second vertebra such that the spine stabilization system permits movement of the first vertebra relative to the second vertebra.

2. The flexible spine stabilization system of claim 1 wherein the slit in the first flexible element forms a helical pattern around a portion of the first rod.

3. The flexible spine stabilization system of claim 1, wherein the second material is a medication.

4. The flexible spine stabilization system of claim 1, wherein the second material is a bioabsorbable elastomer.

5. The flexible spine stabilization system of claim 1, wherein the first flexible element is curved in the neutral position to accommodate the lordosis in the spine.

6. The flexible spine stabilization system of claim 1, wherein the first flexible element limits motion of the first end portion relative to the second end portion from about 1° to about 30° in all planes.

7. The flexible spine stabilization system of claim 1, wherein the first flexible element limits motion of the first end portion relative to the second end portion from about 0° to about 30° in all planes.

8. The flexible spine stabilization system of claim 1, wherein the first flexible element limits rotation of the first end portion relative to the second end portion from about 1° to about 30°.

9. The flexible spine stabilization system of claim 8, wherein the first flexible element limits rotation of the first end portion relative to the second end portion from about 1° to about 6°.

10. The flexible spine stabilization system of claim 1, wherein the first flexible element limits rotation of the first end portion relative to the second end portion from about 0° to about 3°.

11. The flexible spine stabilization system of claim 10, wherein the first flexible element prevents rotation of the first end portion relative to the second end portion.

12. The flexible spine stabilization system of claim 1, wherein the first flexible element limits flexion-extension of the first end portion relative to the second end portion from about 0° to about 30°.

13. The flexible spine stabilization system of claim 12, wherein the first flexible element limits flexion-extension of the first end portion relative to the second end portion from about 0° to about 3°.

14. The flexible spine stabilization system of claim 13, wherein the first flexible element limits flexion-extension of the first end portion relative to the second end portion from about 3° to about 30°.

15. The flexible spine stabilization system of claim 3, wherein the first flexible element limits lateral bending of the first end portion relative to the second end portion from about 0° to about 30°.

16. The flexible spine stabilization system of claim 15, wherein the first flexible element limits lateral bending of the first end portion relative to the second end portion from about 0° to about 3°.

17. The flexible spine stabilization system of claim 15, wherein the first flexible element limits lateral bending of the first end portion relative to the second end portion from about 3° to about 30°.

18. The flexible spine stabilization system of claim 1, wherein the first flexible element limits axial compression of the first end portion relative to the second end portion from about 0 mm to about 7 mm.

19. The flexible spine stabilization system of claim 18, wherein the first flexible element limits axial compression of the first end portion relative to the second end portion from about 0.5 mm to about 7 mm.

20. The flexible spine stabilization system of claim 18, wherein the first flexible element limits axial compression of the first end portion relative to the second end portion from about 0 mm to about 1 mm.

21. The flexible spine stabilization system of claim 20, wherein the depth of the first slit is from about 20 percent to about 99 percent of the radius of the rod.

22. The flexible spine stabilization system of claim 21, wherein the depth of the first slit is from about 50 percent to about 80 percent of the radius of the rod.

23. The flexible spine stabilization system of claim 1, wherein the first flexible element further comprises a second slit formed therein.

24. The flexible spine stabilization system of claim 23, wherein the first slit and the second slit in the first flexible element form helical patterns wound a portion of the first rod.

25. The flexible spine stabilization system of claim 24, wherein at least a portion of the first slit and the second slit are disposed in the same location on the first rod.

26. The flexible spine stabilization system of claim 24, wherein the direction of the helical pattern of the first slit is the same as the direction of the helical pattern of the second slit.

27. The flexible spine stabilization system of claim 24, wherein the direction of the helical pattern of the first slit is opposite from the direction of the helical pattern of the second slit.

28. The flexible spine stabilization system of claim 1, wherein the first flexible element forms at least a portion of a transconnector that connects two longitudinal rods.

29. The flexible spine stabilization system of claim 1, wherein the first and second fasteners are bone fasteners.

30. The flexible spine stabilization system of claim 1, wherein the first slit formed in the first flexible element extends completely through the rod.

31. The flexible spine stabilization system of claim 1, wherein the depth of the first slit is from about 20 percent to about 95 percent of the radius of the rod.

32. The flexible spine stabilization system of claim 31, wherein the depth of the first slit is from about 50 percent to about 80 percent of the radius of the rod.

33. The flexible spine stabilization system of claim 1, further comprising: a second rod having a third end portion and a fourth end portion;
a second flexible element having at least a first slit formed therein,
wherein said second flexible element is disposed between the third and fourth end portions,
wherein the second flexible element is integrally formed between said third and fourth rod portions, and
wherein the second flexible element permits motion of the third end portion relative to the fourth end portion;
wherein the second rod is at least partially disposed between the exterior of the first vertebra and second vertebra.

34. The flexible spine stabilization system of claim 33, wherein the first and second rods permit limited movement of the first vertebra relative to the second vertebra in the antenor-posterior direction and substantially restrict lateral bending.

35. The flexible spine stabilization system of claim 1, further comprising a third fastener capable of connecting with a portion of the first rod, and wherein the third fastener is capable of securely disposing the first rod at least partially between the exterior of the second vertebra and third vertebra.

36. The flexible spine stabilization system of claim 35, wherein the portion of the first rod disposed between the second vertebra and third vertebra substantially restricts movement of the second vertebra relative to the third vertebra.

37. The flexible spine stabilization system of claim 36, wherein the first flexible element permits limited movement of the first vertebra relative to the second vertebra in the anterior-posterior direction and substantially restricts lateral bending.

38. The flexible spine stabilization system of claim 35, wherein the portion of the first rod disposed between the second vertebra and third vertebra is capable of permitting limited movement of the second vertebra relative to the third vertebra.

39. The flexible spine stabilization system of claim 1, wherein the first fastener is a pedicle screw partially disposed in the first vertebra.

* * * * *